(12) United States Patent
De Boer et al.

(10) Patent No.: US 6,346,248 B1
(45) Date of Patent: Feb. 12, 2002

(54) METHODS OF TREATING AUTOIMMUNE DISEASES WITH A CD86-SPECIFIC IMMUNOTOXIN

(75) Inventors: Mark De Boer, Heemskerk; G. C. De Gast, Utrecht, both of (NL)

(73) Assignee: Innogenetics N.V. (NL)

( * ) Notice: Subject to any disclaimer, the term of this patent is extended or adjusted under 35 U.S.C. 154(b) by 0 days.

(21) Appl. No.: 09/373,474

(22) Filed: Aug. 12, 1999

Related U.S. Application Data

(62) Division of application No. 08/973,377, filed as application No. PCT/EP96/02492 on Jun. 7, 1996, now Pat. No. 6,071,519.

(30) Foreign Application Priority Data

Jun. 7, 1995 (EP) .............................................. 95870066

(51) Int. Cl.[7] ........................ A61K 39/395; C07K 16/28
(52) U.S. Cl. ................................ 424/181.1; 424/130.1; 424/133.1; 424/135.1; 424/141.1; 424/143.1; 424/144.1; 424/153.1; 424/173.1; 424/178.1; 424/183.1; 530/387.1; 530/387.3; 530/388.1; 530/388.2; 530/388.22; 530/388.7; 530/388.73; 530/391.1; 530/391.7
(58) Field of Search ........................... 424/130.1, 133.1, 424/143.1, 173.1, 178.1; 530/387.1, 387.3, 388.2, 388.22, 388.73, 391.1, 391.7

(56) References Cited

U.S. PATENT DOCUMENTS

| | | | | |
|---|---|---|---|---|
| 5,872,223 A | * | 2/1999 | Uckun et al. | |
| 6,071,519 A | * | 6/2000 | De Boer et al. | |
| 6,130,316 A | * | 10/2000 | Freeman et al. | |
| 6,146,631 A | * | 11/2000 | Better et al. | |

OTHER PUBLICATIONS

Kahan Cur. Opin Immunol 4: 553–560 (1992).*
Blazar et al. I. Immunol. 157: 3250–3259 (1996).*
Perrin et al. I. Neuroimmunol. 65: 31–39 (1996).*
Yi–Qun et al. Intl. Immunol. 8:37–44 (1996).*

* cited by examiner

*Primary Examiner*—Phillip Gambel
(74) *Attorney, Agent, or Firm*—Bierman, Muserlian and Lucas

(57) ABSTRACT

A method for treating autoimmune diseases comprising administering to a patient in need of such treatment a therapeutically effective amount of an immunotoxin comprising an anti-human CD86 monoclonal antibody IG10H6D10 as deposited in the ECACC collection under No. 95060210 or a humanized antibody, a single-chain antibody or fragments and specificity of said monoclonal antibody, coupled to a toxin or active fragments thereof wherein the binding of the immunotoxin to CD86 results in the killing of the CD86 expressing cell.

4 Claims, 9 Drawing Sheets

METHODS OF TREATING AUTOIMMUNE DISEASES WITH A CD86-SPECIFIC IMMUNOTOXIN

PRIOR APPLICATION

Figure 1:
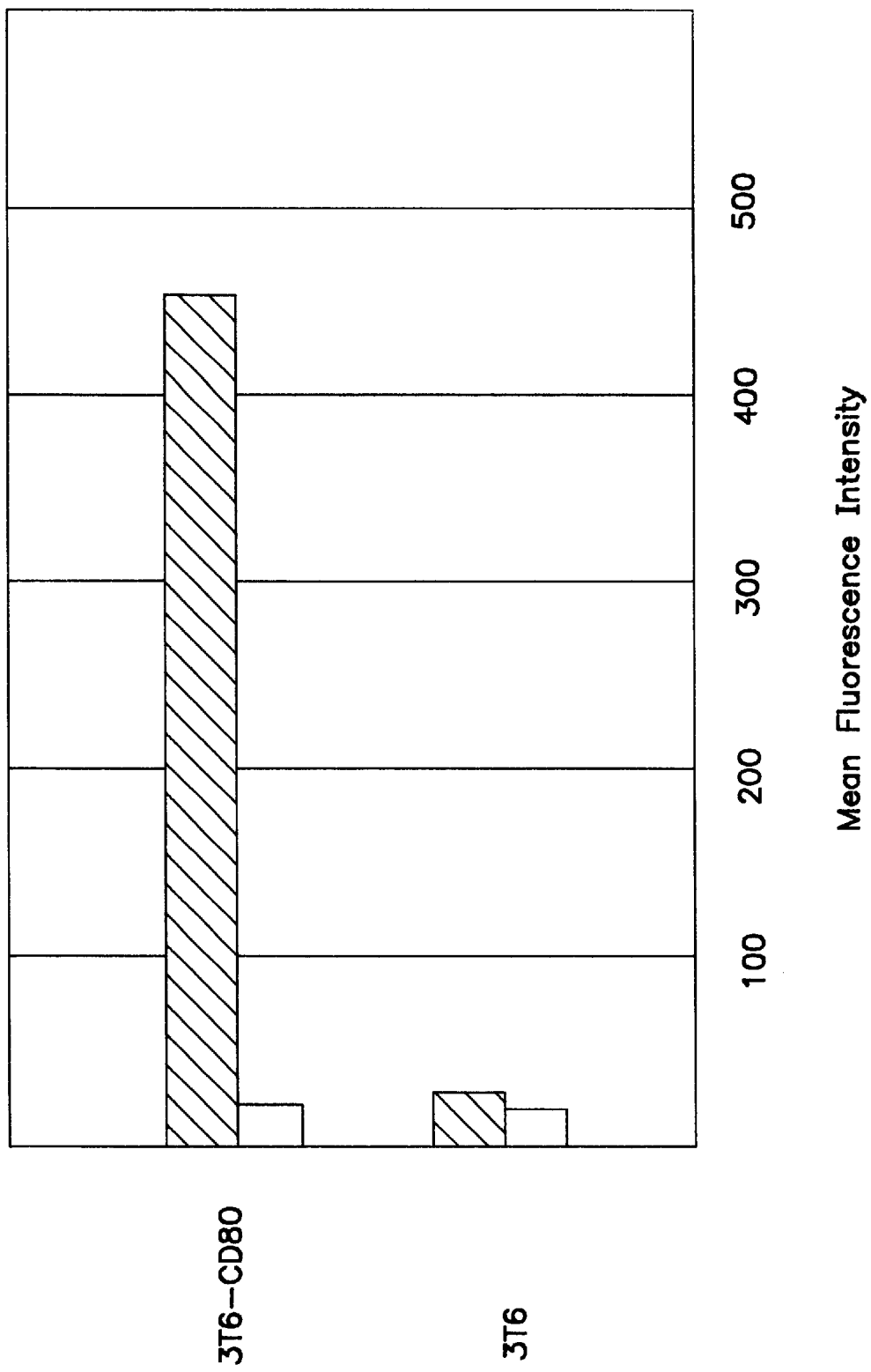

This application is a division of U.S. patent application Ser. No. 08/973,377 filed Dec. 1, 1997, now U.S. Pat. No. 6,071,519 which is a 371 of PCT application No. EP96/02492 filed Jun. 7, 1996.

FIELD OF THE INVENTION

This invention relates to compositions and methods of treating diseases of the immune system. In particular, this invention relates to methods of preventing allograft rejection and methods of treating autoimmune diseases and various malignancies of lymphoid origin.

BACKGROUND OF THE INVENTION

Immunotoxins

Immunotoxins (IT's) are chimeric molecules in which cell-binding ligands are coupled to toxins or their subunits. The ligand portion of the immunotoxin is usually a monoclonal antibody (Mab) that binds to selected target cells. The toxin portion of the immunotoxin can be derived form various sources. Most commonly, toxins are derived from plants or bacteria, but toxins of human origin or synthetic toxins (drugs) have been used as well. Toxins used for immunotoxins derived from plants or bacteria all inhibit protein synthesis of eukaryotic cells. Unlike chemotherapeutic molecules, these toxins kill both resting and dividing cells. The toxins share a number of common features: (i) they are synthesized as single chain proteins and are processed either post translationally or in the target cell to which they are delivered into two-chain molecules with interchain disulfide bonds; (ii) the disulfide bond linking the two chains is critical for cytotoxicity; and (iii) all toxins have separate subunits or domains devoded to binding to cells, translocation across membranes, and the destruction of protein synthesis in the target cell. These domains can be separated or genetically manipulated to delete those that are unwanted.

The most widely used plant toxins ricin and abrin, consist of two disulfate-linked polypeptides A and B (Olsnes et al., in *Molecular Action of Toxins and Viruses* p51–105 (1982)). Another group of plant-derived toxins used in immunotoxins are the ribosome inactivating proteins (RIPs). These molecules are single-chain proteins frequently found in plants and have similar enzymatic properties as the A-chain of ricin (reviewed in Stirpe and Barbieri *FEBS* 195:1 (1986)). The cross-linker used to join the Mab and the toxin must remain stable extracellularly, but labile intracellularly so that the toxin fragment can be released in the cytosol. The choice of cross-linker depends on whether intact toxins, A-chains or RIPs are used. A-chains and RIPs are generally coupled to the Mab using linkers that introduce a disulfide bond between the ligand and the A-chain (Myers et al., *J. Immunol. Meth.* 136:221 (1991)). Bonds that cannot be reduced render these immunotoxins much less toxic or nontoxic, probably because the A-chain must be released from the ligand by reduction to be cytotoxic. Intact toxins are usually linked to ligands using non-reducible linkages (such as thioether) to prevent release of the active free toxin in vivo.

RIPs, efficiently inhibit eukaryotic protein synthesis. Gelonin is a type I RIP (single catalytic chain), which has an advantage above type II RIPs in that type II RIPs have in addition to the catalytic chain, a cell-binding lectin-like B-chain. Because gelonin has no cell-binding lectin-like B-chain, it is unable to bind to cell membranes in the absence of a targeting agent and therefore has a low non-specific toxicity. Even in comparison with another type I RIP (saporin), LD50 studies in mice have shown that native gelonin is approximately 10-fold less toxic than saporin, and thus may be particularly suitable for therapeutic applications. Moreover, immuno-conjugates with gelonin when targeted to cells have low IC50 values, inhibit a greater percentage of target cells and require less exposure time in comparison to other toxins. For these reasons, the low native toxicity and the high specific toxicity, the therapeutic window is very high for gelonin. Gelonin is among the most promising toxins used for the construction of ITs. In direct comparison experiments, gelonin was superior to two of the most popular toxins, ricin A chain and Pseudomonas exotoxin A (Fishwild et al *Clin Exp Immunol* 97:10 (1994)). The cDNA of gelonin was recently isolated (Better et al *J Biol Chem* 270:14,951 (1995)), allowing the construction of single chain antibody-toxin fusion proteins (ScFv-IT). A complete Mab consists of two complete heavy and two complete light chains and has a molecular weight of 150 kDa. An immunotoxin molecule based on a whole antibody will have a molecular weight in the range of 200 kDa, depending on the type of toxin and the amount of toxin molecules coupled per antibody. A single chain antibody fragment (ScFv) however, consists of only the variable part of the heavy and light chain coupled via a short linker and has a molecular weight of approximately 25 kDa. When a toxin molecule is directly fused to a ScFv molecule by genetic engineering, the size of the ScFv-immunotoxin molecule thus obtained, will be a factor 4 smaller when compared to a complete antibody-immunotoxin molecule. Since tumor penetration is mainly dependent on size (the smaller the IT the better the tumor penetration), it is preferred to use ScFv-IT molecules. In addition, the serum half-live of a ScFv-IT is much shorter when compared to a complete antibody-immunotoxin molecule, thus reducing the non-specific systemic toxicity.

CD80/CD86 Costimulatory Molecules

CD80 (B7.1) is a monomeric transmembrane glycoprotein with an apparent molecular mass of 45–65 kDa and is a member of the immunoglobulin superfamily (Freeman et al. *J. Immunol.* 143:2714, (1989)). It was initially reported that the expression of the CD80 molecule was restricted to activated B cells (Freeman et al., *J. Immunol.* 143:2714, (1989)) and monocytes stimulated with IFN-γ (Freedman et. al., *Cell. Immunol.* 137:429, (1991)). More recently, CD80 expression has also been found on cultured peripheral blood dendritic cells (Young et al. *J. Clin. Invest.* 90: 229 (1992)). The expression of the CD80 molecule in a number of normal and pathological tissues has been examined by immunohistochemistry using an anti-CD80 monoclonal antibody (Vandenberghe et al., *Int. Immunology* 5:317 (1993)). In addition to the staining of activated B cells, it was shown that the CD80 molecule is constitutively expressed in vivo on dendritic cells in both lymphoid and non-lymphoid tissue. Monocytes/macrophages were only found to be positive under inflammatory conditions and endothelial cells were always negative. Interestingly, the number of CD80 positive cells in skin lesions of patients with acute GVHD was strongly increased when compared to normal skin. This expression pattern of CD80 on different antigen presenting cells (APCs), strongly suggests an important costimulatory role in T-cell activation.

It has recently been demonstrated that CD80 is a member of a family of closely related molecules molecules, that can functionally interact with CD28 (Hathcock et al. *Science* 262:905 (1993); Freeman et al. *Science* 262:907 (1993); Azuma et al. *Nature* 366:76 (1993)). The second member of this family, B7.2 or CD86, is also a transmembrane glycoprotein, with an apparent molecular mass of approximately 70 KDa and is also a member of the immunoglobulin superfamily (Freeman et al. *Science* 262:907 (1993); Azuma et al. *Nature* 366:76 (1993)). The CD86 molecule seems to have a very similar distribution pattern as CD80, with the exception that induction of cell-surface expression seems to be faster and that it is present on freshly isolated monocytes.

Transplant Rejection

Incompatibility for the histocompatibility antigens, both major (MHC) and minor antigens, is the cause for graft rejection. Both CD4+ helper T cells (Th) and CD8+ cytotoxic T cells (CTL) are involved in the rejection process. Activation of T cells after transplantation is the result of ligand-receptor interactions, when the TcR/CD3 complex recognizes its specific alloantigen in the context of the appropriate MHC molecule. To induce proliferation and maturation into effector cells, T cells need a second signal in addition to the one mediated by the TcR/CD3 complex. Intercellular signaling after TcR/MHC-peptide interaction in the absence of the costimulatory signal results in T-cell inactivation in the form of clonal anergy (Mueller et al. *Annu. Rev. Immunol.* 7:445 (1989)). It has been demonstrated that blocking CD80/CD86, when combined with a donor-specific cell transfusion, can prevent the rejection MHC-mismatched cardiac allografts in a rat model (Lin et al. *J. Exp. Med.* 178:1801 (1993)). In addition, it has been demonstrated that co-stimulation of T cells via the crosslinking CD28 is resistant to the inhibitory activity of the immunosuppressive drug cyclosporin A (June et al. *Immunol. Today* 11:211 (1990)). This demonstrates the importance of the CD80/CD86-CD28 interaction in the rejection of transplants. It has been suggested and demonstrated in rodent models, that blocking both CD80 and CD86, thereby preventing the ligation of CD28 on T cells, can prevent rejection of allo-transplants. However, no prior art exists that an immunotoxin targeting CD80 or CD86 can prevent alloantigen-specific T cell activation and thus allo-graft rejection.

Autoimmune Diseases

A number of studies indicate that costimulation through CD28 ligation might be the initiating event in autoimmunity. The potential of both a primary signal via the TcR and CD80 as a costimulatory signal for the generation of autoimmune diabetes has clearly been proven with transgenic mice (Guerder et al., *Immunity* 1:155 (1994); Harlan, et al., *PNAS* 91:3137 (1994)). In these studies, it is hypothesized that tolerance to peripheral antigens is induced by triggering the TcR in the absence of essential costimulatory signals. Mice expressing both CD80 and a high level of primary antigens (MHC molecules or viral glycoproteins) on pancreatic beta cells developed autoimmune diabetes. The critical role of the absence of CD80-mediated costimulation in the induction and maintenance of tolerance to peripheral antigens, and of the CD80-mediated signalling in the breakdown of T-cell nonresponsiveness, causing autoimmunity, was obvious.

The role of the CD80/CD86-CD28 interaction in the chronic activation state of T cells, which have been implicated in autoimmune diseases, has been strongly suggested in various studies. Using immunohistochemical techniques, strong CD80 expression has been found in lesions of autoimmune diseases, such as rheumatoid arthritis and psoriasis. Furthermore, it has been demonstrated that blocking CD80/CD86-CD28 interaction could block autoantibody production and prolongation of life in a murine model of autoimmune disease that closely resembles systemic lupus erythematosus in humans (Finck et al., *Science* 265:1225 (1994)).

Hodgkin's Disease

Hodgkin's Disease (HD) comprises a group of malignant lymphomas with common clinical and pathologic features. The diagnosis is based on a disrupted lymph node architecture and the presence of the presumed malignant mononucleated Hodgkin and the multinucleated Reed-Stemberg (H-RS) cells in the right setting, consisting mainly of small lymphocytes, and a variable admixture of histiocytes, eosinophils and plasma cells. The etiology of HD and the origin of the H-RS cells remains unclear. Four histologic subtypes are recognized: Lymphocytic predominance (5–10%), nodular sclerosis (40–70%), mixed cellularity (20–40%) and lymphocytic depletion (5%). Prognosis is mainly determined by the stage of the disease as determined according to Ann-Arbor classification. An unbalanced production of cytokines in active HD has been associated with constitutional "B" symptoms as fever, night sweats, generalized itching and weight loss.

Immunohistology of HD lymph nodes shows that the majority of T cells surrounding the H-RS cells are activated (IL-2R+, CD40L+) CD4+ memory T cells H-RS cells express strongly CD30, CD40, IL-2R, CD80, CD86, CD71 (Transferrin Receptor) and adhesion molecules such as ICAM-1. Cytokines produced by H-RS cell lines include IL-6, IL-8, TNF-alpha, TNF-beta or lymphotoxin, GM-CSF, IL-1, IL-3, IL-10 and TGF-beta. These cytokines are very likely responsible for the clinical features of HD like eosinophilia, "B" symptoms, acute phase reactants, thrombocytosis and sclerosis of HD involved tissues. HD is a tumor highly responsive to both chemotherapy and radiotherapy. Most patients with early stage disease can be cured with single modality treatment. The majority of patients presenting with advanced disease can also achieve complete remission. However a significant proportion (about 40%) of patients will have recurrence of their disease. For patients not attaining a complete remission on first and second line chemotherapy initially or at relapse the outcome is dismal. Although responses to salvage regimens are present, long term disease-free survival is unusual with only 20% 5 year survival. In patients relapsing after chemotherapy intensive chemotherapy followed by autologous bone marrow transplantation seems to be a good option in those with a sensitive relapse, but long term results have to be awaited. A further concern are secondary tumors and heart disease in patients cured from HD, probably due to toxicity of the chemo- and/or radio-therapy. Immunotherapy may be a good alternative initially in HD patients with primary resistant disease or relapse, and if successful probably also in patients with earlier stages of HD.

Problems Posed in the Present Invention

As is reviewed above, it is known that certain surface molecules are upregulated or overexpressed in diseases of the immune system. A specific example of such molecules are CD80 and CD86 present on antigen presenting cells (APCs). A number of these upregulated surface antigens have been proven to be involved in T cell-activation. For the treatment of diseases of the immune system which involve these surface antigens, researchers have focused on ways to block these surface antigen molecules (e.g. by using Mab directed to these surface antigen molecules) so that they cannot function normally because they cannot transmit the necessary signal to the T-cell.

The problem posed in the present invention may be formulated as providing an alternative method for treating or preventing diseases of the immune system, more particularly for treating or preventing allograft rejection, autoimmune diseases and various malignancies of lymphoid origin.

To solve this problem the present inventors have been able to prove that immunotoxins can, surprisingly, also be used in the field of treating diseases of the immune system, more particularly for treating allograft rejection, autoimmune diseases and malignancies of lymphoid origin such as Hodgkin's disease. It should be stressed that the use of immunotoxins is well known in the field of treating tumors. Surprisingly, however, the present inventors could show that the technology of immunotoxins could also be applied in a way that it indirectly influences the activation state of T-cells, implying that the inhibition of protein synthesis in one cell type, the antigen presenting cell, has an effect on a second cell type, the antigen-specific T-cell. This is surprising, since protein expression for essential costimulatory molecules such as CD80 and CD86 on the antigen-presenting cells is not immediately eliminated. In other words, only de novo synthesized CD80/CD86 molecules appear to be essential to activate T cells and not the CD80/CD86 molecules which were present before, or immediately after, the addition of immunotoxins.

This alternative method for blocking the interaction between APC's and T cells based on the usage of CD80/CD86 immunotoxins shows a considerable advantage over the existing methods using anti-CD80/86 Mab's in a way that killing the APC's, instead of only blocking the CD80/86 molecules, also inhibits signalling from other accessory molecules (such as LFA-1, LFA-3, ICAM or others) on the APC's which are known, in addition to CD80 and CD86, to be involved in T cell triggering (van Gool et al. *Res. Immunol* 146:183 (1995)). Furthermore, it is also known that both CD80 and CD86 are important in T cell triggering by APC's (van Gool et al. *Res. Immunol.* 146:183 (1995) which implies that both molecules need to be blocked to efficiently inhibit T cell activation. The approach using Mab's would therefore involve the usage of at least two different Mab's (anti-CD80 and anti-CD86) whereas only one immunotoxin (CD80-IT or CD86-IT) can be used following the alternative method of the present invention.

It is further known that radioimmunoconjugates and immunotoxins are largely unexplored in Hodgkin's Disease. Only preliminary studies have been reported. Yttrium-labeled anti-ferritin and CD30-saporin have shown promising results in phase I–II studies in end stage patients with HD. Radio-immuno-therapy has the disadvantage of considerable hematologic toxicity, difficulties with dosing and the fact that HD patients have already received significant amounts of radiation. The CD30-immunotoxin is a much more focussed approach directed to Hodgkin/Reed-Stemberg (H-RS) cells. One small trial is reported using ITs in HD (Falini et al *Lancet* 339:1195 (1992)). In this trial, 4 chemotherapy resistant patients were treated with CD30-saporin bolus infusions (06 mg/kg I.V. in one or two doses). No severe toxicity was observed. Patients suffered from minor episodes of fever, malaise, anorexia, minor liver function disturbances and thrombocytopenia with no Vasicular Leak Syndrome (VLS) or hypo-albuminemia. No maximum tolerated dose was established. While toxicity was limited, ¾ patients achieved a transient remission and a minimal response. CD30 may not be an ideal antigen for an immunotoxin in HD. This is because soluble CD30 is present in the blood of patients with advanced HD (Gause, et al., *Blood* 77:1983 (1991)) and this antigen is also expressed on activated T cells, which are present in large numbers in HD. Elimination of these cells by a CD30-immunotoxin may aggravate the already existing T cell function defects in HD and can cause a T cell cytokine release syndrome.

Target antigens for potential ITs, strongly expressed on H-RS cells are as indicated above CD30, CD40, IL-2 receptor (CD25), CD80, CD86 and the Transferrin-Receptor (CD71). An anti-CD80-IT or anti-CD86-IT is clearly the best, because of the anticipated side effects of the others. CD71 is a poor target antigen because it is expressed on all rapidly dividing cells. Bone marrow toxicity is a significant problem with an anti-CD71-IT (See example 6 below). Anti-CD40-IT will eliminate all (resting and activated) B cells and activated endothelial cells. In addition, anti-CD-40-IT generate monokine release and anti-CD30-IT and anti-CD25-IT will augment T lymphokine release. Furthermore, soluble forms of CD25, CD30 and CD40, present in HD patients, complicate dosing and reduce efficacy. Using anti-CD80-IT and anti-CD86-IT might result in the elimination of activated dendritic cells. This will be only transient, as these cells will be rapidly replaced from stem cells. As a matter of fact, elimination of the dendritic cells by anti-CD80-IT and anti-CD86-IT even has a positive effect, since antigen presentation is blocked and therefore the capacity of the patient to produce antibodies to the immunotoxin response is blocked. The CD80 and CD86 antigens are thus likely the best antigens for several reasons: (i) antigen heterogeneity, most HD tumors express CD80 and/or CD86; (ii) soluble forms of CD25, CD30 and CD40 complicate dosing and reduce efficacy; (iii) antigen modulation (i.e. cleavage from the cell membrane by proteases) of molecules such as CD25, CD30 and CD40 negatively influences uptake of IT's into the cells; (iv) there will be no antibody response to anti-CD80-IT and anti-CD86-IT.

In this regard, the problem posed in the present invention may be regarded as chosing suitable surface molecules which would direct immunotoxins to the malignant types of cells present in patients suffering from Hodgkin's Disease.

To solve this problem the present inventors have been able to prove that surprisingly CD80 and/or CD86 can be used to design anti-CD80 toxin conjugates and/or anti-CD86 toxin conjugates which can effectively be used in vitro to inhibit the growth of tumor cell lines (example 6). From this finding it could be concluded that such immunotoxins can also be used to treat Hodgkin's disease in vivo.

In short, the present invention aims particularly at providing new immunotoxins or compositions comprising the same, methods for preparing the same and methods for treating diseases of the immune system involving the use of these immunotoxins or compositions.

The invention also aims at providing a medicament comprising the same as well as a method for preparing said medicament.

In particular, the present invention aims at methods for preventing allograft rejection.

More particularly, the present invention aims at methods for treating autoimmune diseases.

Also, the present invention aims at providing methods for treating various malignancies of lymphoid origin, more particularly Hodgkin's disease.

Also, the present invention aims at providing donor organs and isolated lymphocytes incubated ex vivo with said immunotoxins or said compositions, as well as a method for their preparation.

All the aims of the present invention are considered to have been met by the embodiments as set out below.

SUMMARY OF THE INVENTION

The current invention is based on the discovery that conjugates of antibodies to human CD80 or human CD86 and a toxin can effectively kill cells expressing these molecules. Accordingly, these antibody-toxin conjugates (which are referred to as "immunotoxins" throughout the remainder of the invention) can be used to prevent or treat (terms used interchangedly) diseases or conditions that are directly or indirectly mediated by the target molecules of the immunotoxin or by the cells carrying the target molecules.

More particularly, the present invention relates to an immunotoxin molecule comprising an antibody specific for human CD80 or CD86 antigen located on the surface of a human cell, coupled to a toxin molecule or active fragment thereof, wherein the binding of the immunotoxin to the CD80 or CD86 antigen results in the killing of the CD80 or CD86 expressing cell.

More particularly, the present invention relates to an immunotoxin molecule comprising an antibody specific for the human CD80 antigen located on the surface of a human cell, coupled to a toxin molecule or active fragment thereof, wherein the binding of the immunotoxin to the CD80 antigen results in the killing of the CD80 expressing cell.

More particularly, the present invention relates to an immunotoxin molecule comprising an antibody specific for the human CD86 antigen located on the surface of a human cell, coupled to a toxin molecule or active fragment thereof, wherein the binding of the immunotoxin to the CD86 antigen results in the killing of the CD86 expressing cell.

According to a possible embodiment, the present invention relates to an immunotoxin comprising an antibody specific for human CD80 and human CD86 both located on the surface of a human cell, coupled to a toxin molecule or active fragment thereof, wherein the binding of the immunotoxin to the CD86 and CD80 antigen results in the killing of the CD80 and CD86 expressing cell.

According to a preferred embodiment, the invention provides an immunotoxin molecule as defined above, wherein said toxin is saporin, gelonin, Pseudomonas exotoxin or Pokeweed antiviral protein or an active fragment thereof.

According to a most preferred embodiment, the invention provides an immunotoxin molecule as defined above, wherein said toxin is gelonin or an active fragment thereof.

According to a preferred embodiment, the invention provides an immunotoxin as defined above, wherein said antibody is a monoclonal antibody or preferably a humanized antibody or a single-chain antibody or a fragment derived from said monoclonal antibody which all have largely retained the specificity of said monoclonal antibody.

According to a preferred embodiment, the present invention relates to immunotoxin molecule as defined above, wherein said monoclonal antibody is the anti-human CD80 monoclonal antibody 5B5D1 as deposited in the ECACC (European Collection of Cell Cultures) collection under No. 95060211 on Jun. 2, 1995 or a humanized antibody, a single-chain antibody or fragments thereof which have largely retained the specificity of said monoclonal antibody.

According to an even preferred embodiment, the present invention provides an immunotoxin molecule as defined above, wherein said monoclonal antibody is the anti-human CD86 monoclonal antibody 1G10H6D10 as deposited in the ECACC collection under No. 95060210 on Jun. 2, 1995 or a humanized antibody, a single-chain antibody or fragments thereof which have largely retained the specificity of said monoclonal antibody.

According to an even more preferred embodiment, the present invention relates to an immunotoxin as defined above, wherein said single chain antibody and said toxin are encoded by a single recombinant DNA (nucleic acid) molecule. This type of recombinant DNA molecule will be named a "recombinant immunotoxin of the invention".

The present invention particularly contemplates recombinant immunotoxin fusion proteins (containing a nucleic acid encoding part of the variable region of the monoclonal antibody fused in frame to a nucleic acid encoding part of a toxin molecule) inspired on the anti-human CD80 monoclonal antibody 5B5D1 as deposited in the ECACC (European Collection of Cell Cultures) collection under No. 95060211 on Jun. 2, 1995 and of the anti-human CD86 monoclonal antibody 1G10H6D10 as deposited in the ECACC collection under No. 95060210 on Jun. 2, 1995.

The present invention also contemplates said recombinant immunotoxin DNA molecule.

The present invention also contemplates recombinant vectors comprising a nucleic acid sequence encoding the amino acid sequence of such a single chain antibody-toxin fusion product (recombinant immunotoxin).

The present invention also contemplates hosts cells transformed by such a vector (and expressing said recombinant immunotoxin).

According to yet another embodiment, the present invention relates to a method for producing an immunotoxin as defined above comprising the steps of chemically or enzymatically coupling a ligand portion consisting of an anti-human CD80 or anti-human CD86 antibody or a derivative thereof as defined above to a toxin portion or a fragment thereof as defined above and isolating the conjugates from the non-conjugated material by any method known in the art.

According to yet another embodiment, the present invention relates to a method for producing a recombinant immunotoxin as defined above comprising the steps of culturing a host cell as defined above which is transformed with a vector comprising a nucleic acid sequence encoding said recombinant immunotoxin under suitable conditions and purifying said immunotoxin by any method known in the art.

According to another embodiment, the present invention provides a composition comprising an immunotoxin molecule as defined above in a pharmaceutically acceptable excipient for use in therapy (this type of compositions is referred to as "composition comprising the same" throughout the remainder of the invention).

According to yet another embodiment, the present invention provides a medicament comprising an immunotoxin molecule as defined above.

According to another embodiment, the present invention provides an immunotoxin molecule or a composition comprising the same as defined above for use as a medicament.

According to still another embodiment, the present invention relates to the use of an immunotoxin molecule or a composition comprising the same for the preparation of a medicament for treating diseases of the immune system, in particular for preventing allograft rejection, treating autoimmune diseases and treating various malignancies of lymphoid origin such as Hodgkin's Disease (the term "treating" is to be understood as referring to the treatment of a patient suffering from a disease as well as to the prophylactic or preventive treatment of an individual liable to suffer from a disease).

According to a particularly preferred embodiment, the present invention relates to a method for preventing allograft transplant rejection, the method comprising administering to a patient in need of such treatment a therapeutically effective amount of an immunotoxin or a composition comprising the same as defined above, wherein the binding of the immunotoxin to the CD80 or CD86 antigen prevents the activation and differentiation of host T-cells against the MHC on the allograft, in a pharmaceutically acceptable excipient.

According to a particularly preferred embodiment, the present invention provides an immunotoxin or a composition comprising the same as defined above for use in a method for preventing allograft transplant rejection, the method comprising administering to a patient in need of such treatment a therapeutically effective amount of such an immunotoxin or such a composition, wherein the binding of the immunotoxin to the CD80 or CD86 antigen prevents the activation and differentiation of host T-cells against the MHC on the allograft, in a pharmaceutically acceptable excipient.

According to a preferred embodiment, the present invention provides for the use of an immunotoxin or a composition comprising the same as defined above for the preparation of a medicament for preventing allograft transplant rejection.

According to a further embodiment, the present invention provides a method for preventing allograft transplant rejection, the method comprising administering to a patient in need of such treatment a therapeutically effective amount of an immunotoxin or a composition comprising the same, wherein the binding of the immunotoxin to the CD80 antigen prevents the activation and differentiation of host T cells against the MHC on the allograft, in a pharmaceutically acceptable excipient.

According to yet another embodiment, the present invention provides a method for preventing allograft transplant rejection, the method comprising administering to a patient in need of such treatment a therapeutically effective amount of an immunotoxin or a composition comprising the same, wherein the binding of the immunotoxin to the CD86 antigen prevents the activation and differentiation of host T cells against the MHC on the allograft, in a pharmaceutically acceptable excipient.

According to another embodiment, the present invention provides a method for preventing allograft transplant rejection, the method comprising ex vivo perfusion of a donor organ with a therapeutically effective amount of an immunotoxin or a composition comprising the same as defined above, wherein the binding of the immunotoxin to the CD80 or CD86 antigen results in the killing of said CD80 or CD86 expressing cells.

According to another embodiment, the present invention provides an immunotoxin or composition comprising the same as defined above for use in a method for preventing allograft transplant rejection, the method comprising ex vivo perfusion of a donor organ with a therapeutically effective amount of an immunotoxin or such a composition, wherein the binding of the immunotoxin to the CD80 or CD86 antigen results in the killing of said CD80 or CD86 expressing cells.

According to another embodiment, the present invention relates to the use of an immunotoxin or a composition comprising the same as defined above for the preparation of medicament for preventing allograft transplant rejection involving ex vivo perfusion of a donor organ with a therapeutically effective amount of said immunotoxin or said composition.

According to yet another embodiment, the present invention relates to a method for preventing allograft transplant rejection, the method comprising ex vivo perfusion of a donor organ with a therapeutically effective amount of an immunotoxin or a composition comprising the same, wherein the binding of the immunotoxin to the CD80 antigen results in killing of said CD80 expressing cells.

According to an alternative embodiment, the present invention relates to a method for preventing allograft transplant rejection, the method comprising ex vivo perfusion of a donor organ with a therapeutically effective amount of an immunotoxin or a composition comprising the same, wherein the binding of the immunotoxin to the CD86 antigen results in the killing of said CD86 expressing cells.

According to another embodiment, the present invention relates to a donor organ which has been ex vivo perfused with a therapeutically effective amount of an immunotoxin or a composition comprising the same.

According to an alternative embodiment, the present invention relates to a method for producing a donor organ as defined above, comprising the step of ex vivo perfusion of said donor organ with a therapeutically effective amount of an immunotoxin or a composition comprising the same.

According to another embodiment, the present invention relates to isolated lymphocytes which have been incubated ex vivo with a therapeutically effective amount of an immunotoxin or a composition comprising the same.

According to yet another embodiment, the present invention relates to a method for producing isolated lymphocytes as defined above, comprising the step of ex vivo incubating said isolated lymphocytes with a therapeutically effective amount of an immunotoxin or a composition comprising the same as defined above.

According to yet another embodiment, the present invention provides a method for induction of alloantigen-specific tolerance, the method comprising administering to a patient in need of such treatment a therapeutically effective amount of lymphocytes from an organ donor that have been incubated ex vivo with a therapeutically effective amount of an immunotoxin or such a composition, wherein the binding of the immunotoxin to the CD80 or CD86 antigen results in the killing of said CD80 or CD86 expressing cells, in a pharmaceutically acceptable excipient.

According to another embodiment, the present invention relates to an immunotoxin or a composition comprising the same as defined above for use in a method for induction of alloantigen-specific tolerance, the method comprising administering to a patient in need of such treatment a therapeutically effective amount of lymphocytes from an organ donor that have been incubated ex vivo with a therapeutically effective amount of an immunotoxin or a composition comprising the same as defined above, wherein the binding of the immunotoxin to the CD80 or CD86 antigen results in the killing of said CD80 or CD86 expressing cells, in a pharmaceutically acceptable excipient.

According to another embodiment, the present invention relates to the use of an immunotoxin or a composition comprising the same for the preparation of a medicament for induction of allogen-specific tolerance.

According to another alternative embodiment, the present invention relates to a method for induction of alloantigen-specific tolerance, the method comprising administering to a patient in need of such treatment a therapeutically effective amount of lymphocytes from an organ donor that have been incubated ex vivo with a therapeutically effective amount of an immunotoxin or a composition comprising the same, wherein the binding of the immunotoxin to the CD80 antigen results in killing of said CD80 expressing cells, in a pharmaceutically acceptable excipient.

It is another objective of this invention to provide a method for induction of alloantigen-specific tolerance, the method comprising administering to a patient in need of such treatment a therapeutically effective amount of lymphocytes from an organ donor that have been incubated ex vivo with a therapeutically effective amount of an immunotoxin or a composition comprising the same, wherein the binding of the immunotoxin to the CD86 antigen results in killing of said CD86 expressing cells, in a pharmaceutically acceptable excipient.

According to yet another embodiment, the present invention relates to a method for preventing or treating autoimmune diseases such as rheumatoid arthritis and systematic lupus erythematosus in a patient, the method comprising administering to a patient in need of such treatment a therapeutically effective amount of an immunotoxin or a composition comprising the same, wherein the binding of the immunotoxin to the CD80 or CD86 antigen results in elimination of the CD80 or CD86 expressing cells and inhibition of the local inflammatory response, in a pharmaceutically acceptable excipient.

According to yet another embodiment, the present invention relates to an immunotoxin or a composition comprising the same as defined above for use in a method for preventing or treating autoimmune diseases such as rheumatoid arthritis and systematic lupus erythematosus in a patient, the method comprising administering to a patient in need of such treatment a therapeutically effective amount of an immunotoxin or a composition comprising the same, wherein the binding of the immunotoxin to the CD80 or CD86 antigen results in elimination of the CD80 or CD86 expressing cells and inhibition of the local inflammatory response, in a pharmaceutically acceptable excipient.

According to yet another embodiment, the present invention relates to the use of an immunotoxin or a composition comprising the same as defined above for the preparation of a medicament for preventing or treating autoimmune diseases such as rheumatoid arthritis and systematic lupus erythematosus in a patient.

According to yet another embodiment, the present invention relates to a method for preventing or treating autoimmune diseases such as rheumatoid arthritis and systematic lupus erythematosus in a patient, the method comprising administering to a patient in need of such treatment a therapeutically effective amount of an immunotoxin or a composition comprising the same, wherein the binding of the immunotoxin to the CD80 antigen results in elimination of the CD80 expressing cells and, inhibition of the local inflammatory response, in a pharmaceutically acceptable excipient.

According to yet another embodiment, the present invention relates to a method for preventing or treating autoimmune diseases such as rheumatoid arthritis and systematic lupus erythematosus in a patient, the method comprising administering to a patient in need of such treatment a therapeutically effective amount of an immunotoxin or a composition comprising the same, wherein the binding of the immunotoxin to the CD86 antigen results in elimination of the CD86 expressing cells and inhibition of the local inflammatory response, in a pharmaceutically acceptable excipient.

According to another embodiment, the present invention relates to a method for treating malignancies of lymphoid origin such as Hodgkin's disease in a patient, the method comprising administering to a patient in need of such treatment a therapeutically effective amount of lymphocytes from an organ donor that have been incubated ex vivo with a therapeutically effective amount of an immunotoxin or a composition comprising the same, wherein the binding of the immunotoxin to the CD80 or CD86 antigen results in elimination of the CD80 or CD86 expressing tumor cells, in a pharmaceutically acceptable excipient.

According to yet another embodiment, the present invention relates to an immunotoxin or a composition comprising the same for use in a method for treating malignancies of lymphoid origin such as Hodgkin's disease in a patient, the method comprising administering to a patient in need of such treatment a therapeutically effective amount of an immunotoxin or such a composition, wherein the binding of the immunotoxin to the CD80 or CD86 antigen results in elimination of the CD80 or CD86 expressing tumor cells, in a pharmaceutically acceptable excipient.

According to yet another embodiment, the present invention relates to the use of an immunotoxin or a composition comprising the same for the preparation of a medicament for treating malignancies of lymphoid origin such as Hodgkin's disease in a patient.

According to yet another embodiment, the present invention relates to a method for treating malignancies of lymphoid origin in a patient, the method comprising administering to a patient in need of such treatment a therapeutically effective amount of an immunotoxin or a composition comprising the same, wherein the binding of the immunotoxin to the CD80 antigen results in elimination of the CD80 expressing tumor cells, in a pharmaceutically acceptable excipient.

According to yet another embodiment, the present invention relates to a method for treating malignancies of lymphoid origin in a patient, the method comprising administering to a patient in need of such treatment a therapeutically effective amount of an immunotoxin or a composition comprising the same, wherein the binding of the immunotoxin to the CD86 antigen results in elimination of the CD86 expressing tumor cells, in a pharmaceutically acceptable excipient.

According to a particularly preferred embodiment, the present invention relates to a method for treating Hodgkin's disease in a patient, the method comprising administering to a patient in need of such treatment a therapeutically effective amount of an immunotoxin or a composition comprising the same, wherein the binding of the immunotoxin to the CD80 antigen results in elimination of the CD80 expressing tumor cells, in a pharmaceutically acceptable excipient.

According to a particularly preferred embodiment, the present invention relates to a method for treating Hodgkin's disease in a patient, the method comprising administering to a patient in need of such treatment a therapeutically effective amount of an immunotoxin or a composition comprising the same, wherein the binding of the immunotoxin to the CD86 antigen results in elimination of the CD86 expressing tumor cells, in a pharmaceutically acceptable excipient.

These embodiments of the present invention are detailed further in the section "detailed description of the invention".

BRIEF DESCRIPTION OF THE DRAWINGS AND TABLES

FIG. 1: shows that the antibodies secreted by the 5B5D1 hybridoma clone specifically bind to the CD80-expressing 3T6 cells (gray bars), whereas 3T6 cells that do not express CD80 do not exhibit any binding significantly greater than that of the GAM-FITC (open bars).

Figure 2:
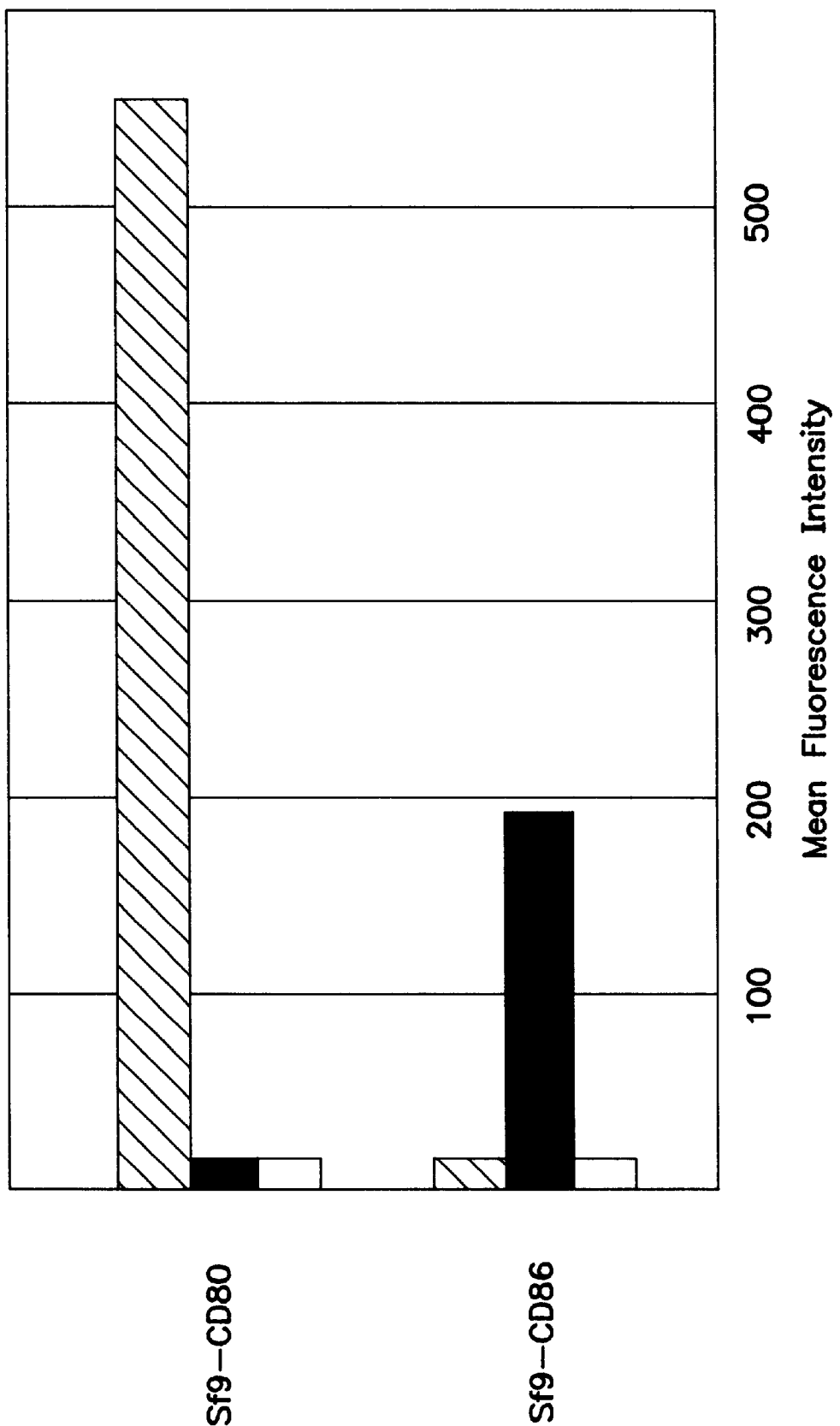

FIG. 2: shows that the antibodies secreted by the 5B5D1 hybridoma clone specifically bind to the CD8-expressing Sf9 cells (gray bars), whereas Sf9 cells expressing the CD86 molecule do not exhibit any binding significantly greater than that of the GAM-FITC (open bars). In contrast, the antibodies secreted by the 1G10H6D10 hybridoma clone specifically bind to the CD86-expressing Sf9 cells (closed bars), whereas Sf9 cells expressing the CD80 molecule do exhibit any binding significantly greater than that of the GAM-FITC (open bars).

Figure 3:
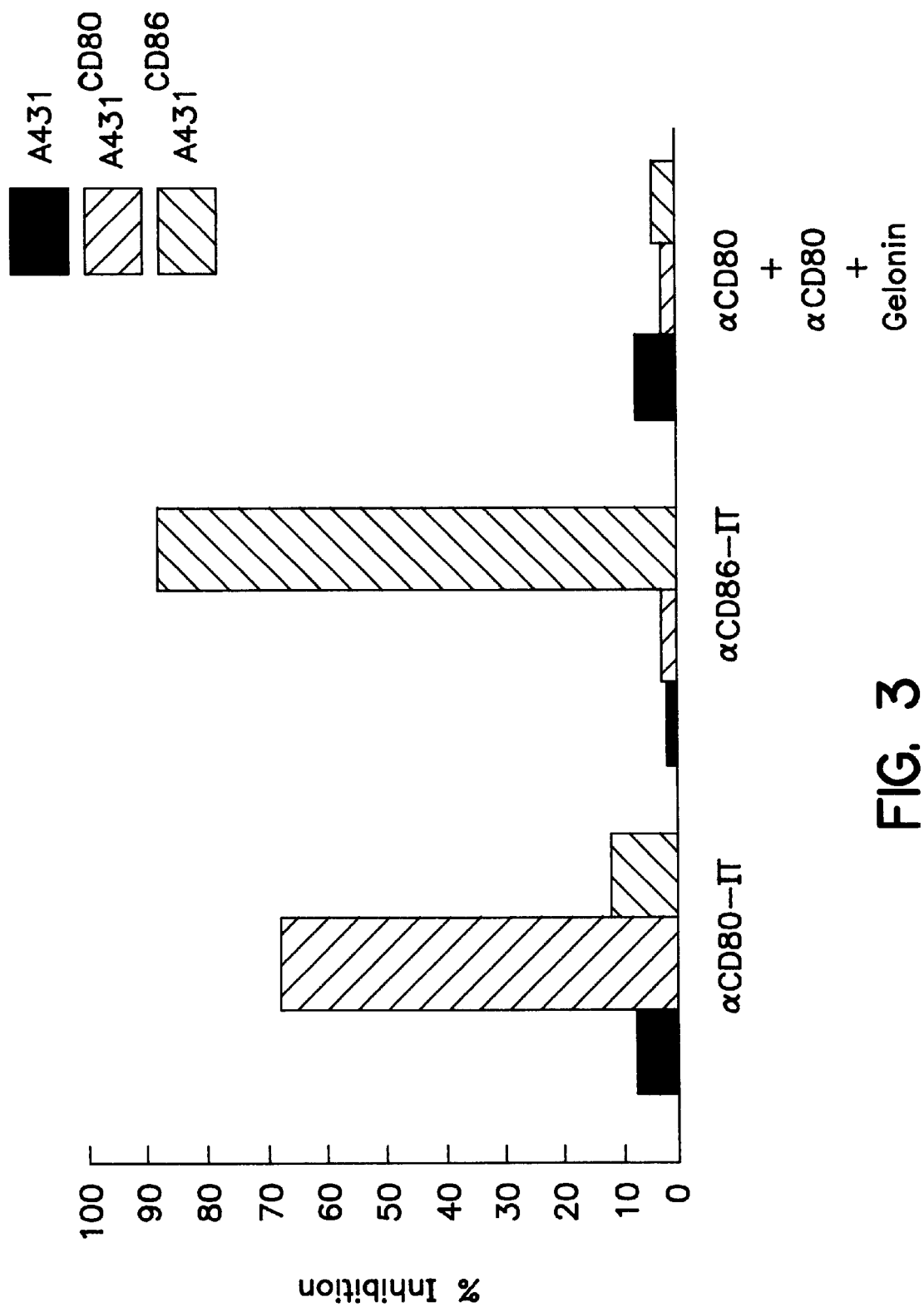

FIG. 3: shows the specificity of the anti-CD80 and anti-D86 gelonin immunotoxins (alpha CD80-IT and alpha CD86-IT). The anti-CD80-gelonin can kill the A431 cells transfected with human CD80 (horizontally-striped bars), as determined by the inhibition of cell proliferation, but not A431 cells transfected with human CD86 (slanted-striped bars) or untransfected cells (closed bars). The anti-CD86 gelonin can kill the A431 cells transferred with human CD86 (slanted-striped bars) but not A431 cells transfected with human CD80 (horizontally-striped bars) or untransfected cells (closed bars). A combination of anti-CD80 Mab, anti-CD86 Mab and free gelonin did not result in the killing of any of the A431 cells.

Figure 4:
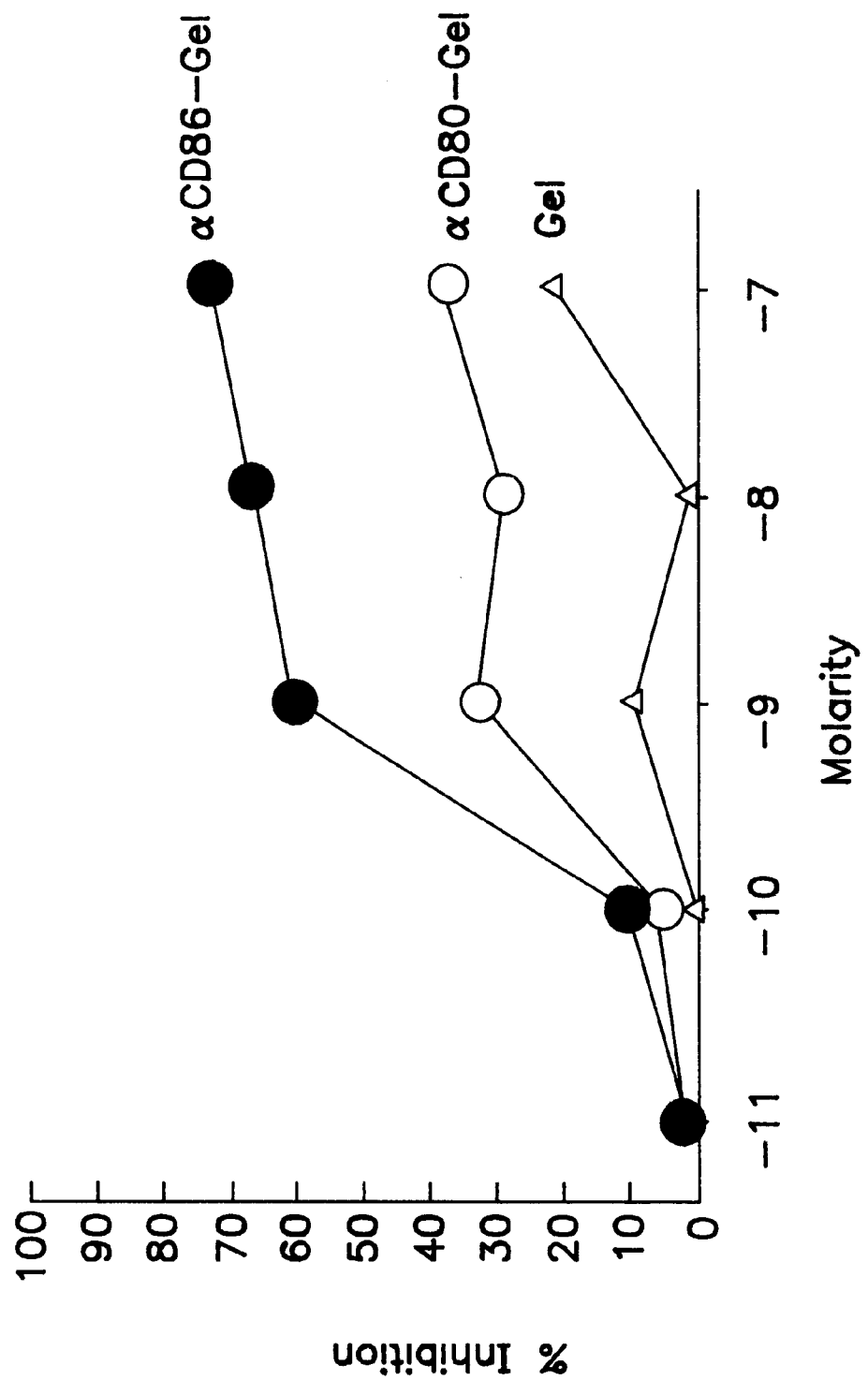

FIG. 4: shows that both anti CD80-gelonin (open circles) and anti CD86-gelonin (closed circles) can dose dependently inhibit the proliferation of alloreactive T cells during a mixed lymphocyte culture, whereas the free toxin only (open triangles (gel)) inhibits the proliferation of the T cells at high concentrations.

Figure 5:
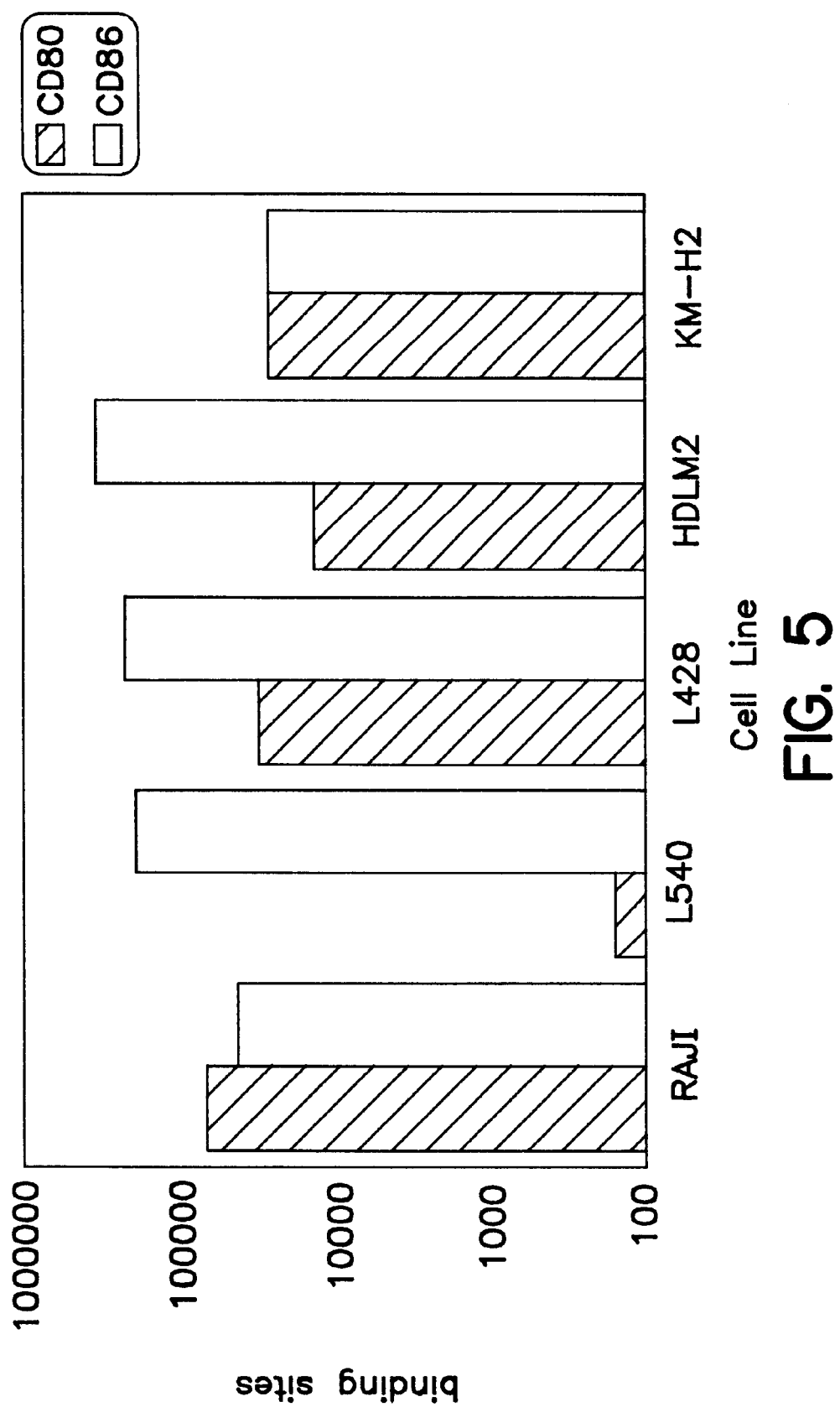

FIG. 5: shows that the Burkitt lymphoma-derived B cell line Raji is positive for both CD80 (slanted-striped bars) and CD86 (open bars) expression. The Hodgkin-derived Reed-Stemberg cell line L540 is negative for CD80 (slanted-striped bars) expression, but positive for CD86 expression (open bars). The Reed-Stemberg cell lines L428, HDLM2 and KM-H2 are positive for both CD80 (slanted-striped bars) and CD86 (open bars) expression.

FIG. 6 A: shows that the growth of the CD80 negative, CD86 positive L540 cells (closed triangles) is not inhibited by incubation with CD80-Saporin. The CD80 and CD86 positive cell lines L428 (closed circles), KM-H2 (closed squares) and Raji (open circles) are killed by CD80-Saporin in a dose dependent fashion.

Figure 6A:
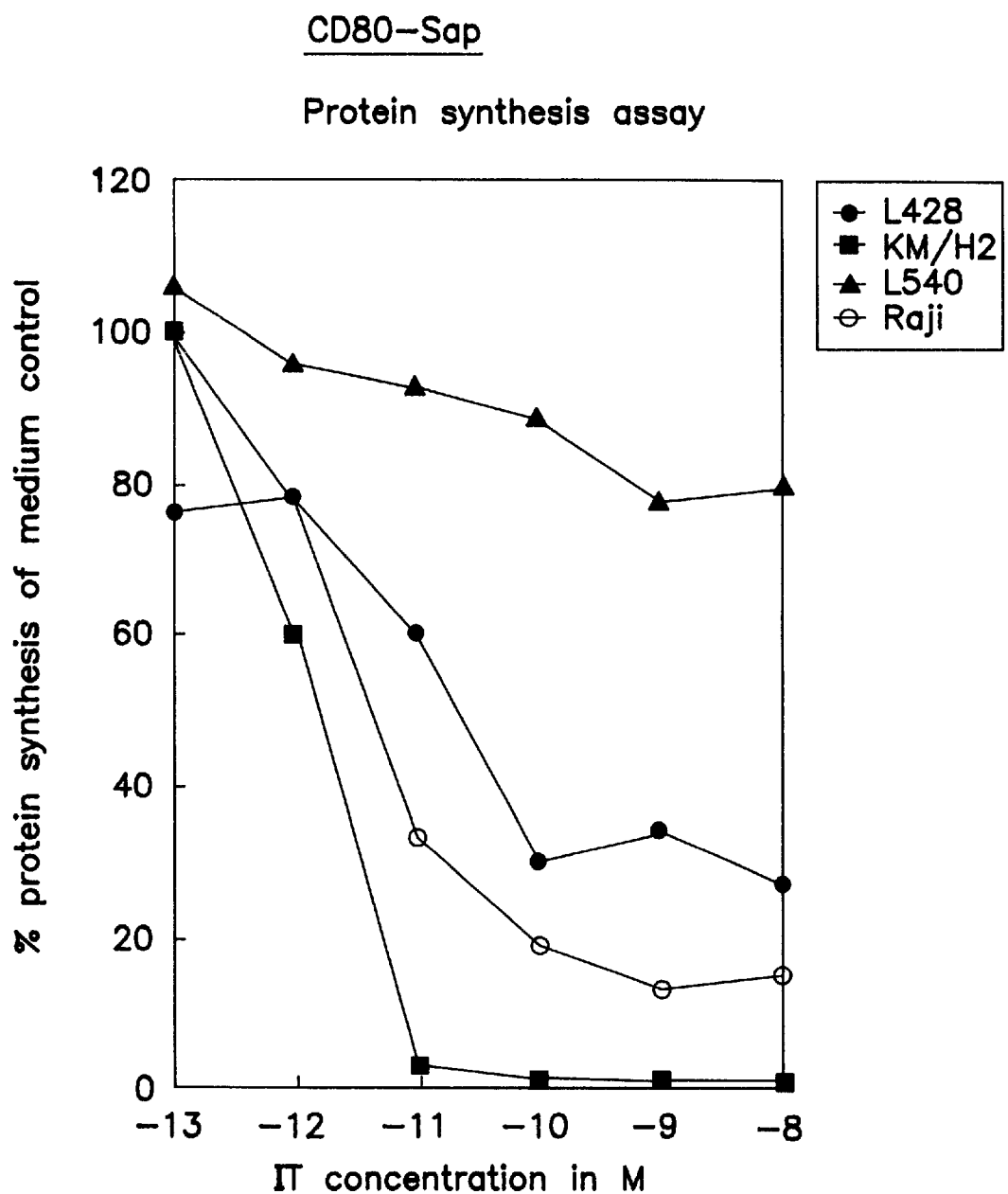
Figure 6B:
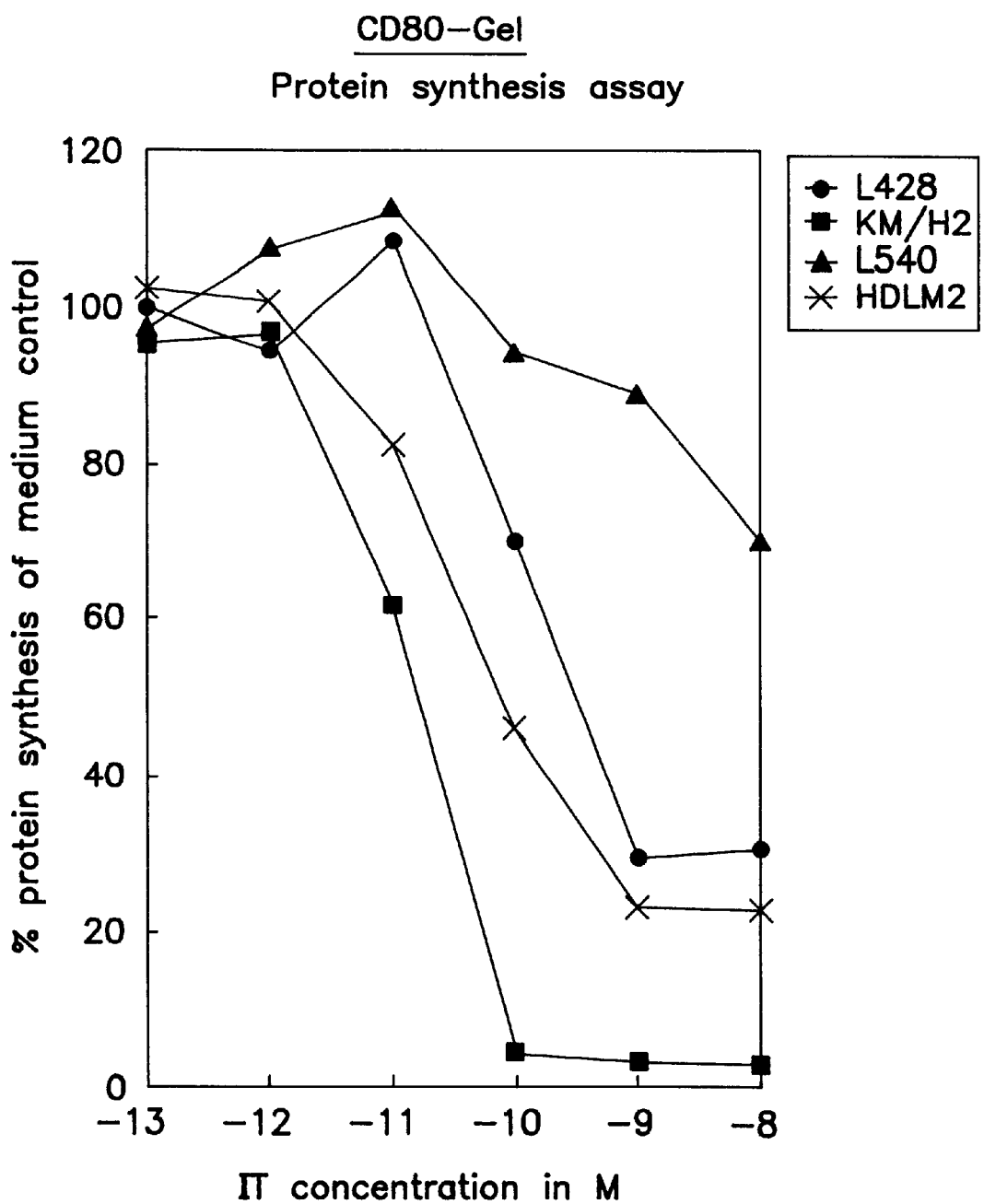

FIG. 6B: shows that the growth of the CD80 negative, CD86 positive L540 cells (closed triangles) is not inhibited by incubation with CD80-Gelonin. The CD80 and CD86 positive cell lines L428 (closed circles), KM-H2 (closed squares) and Raji (open circles) are killed by CD80-Gelonin in a dose dependent fashion.

Figure 6C:
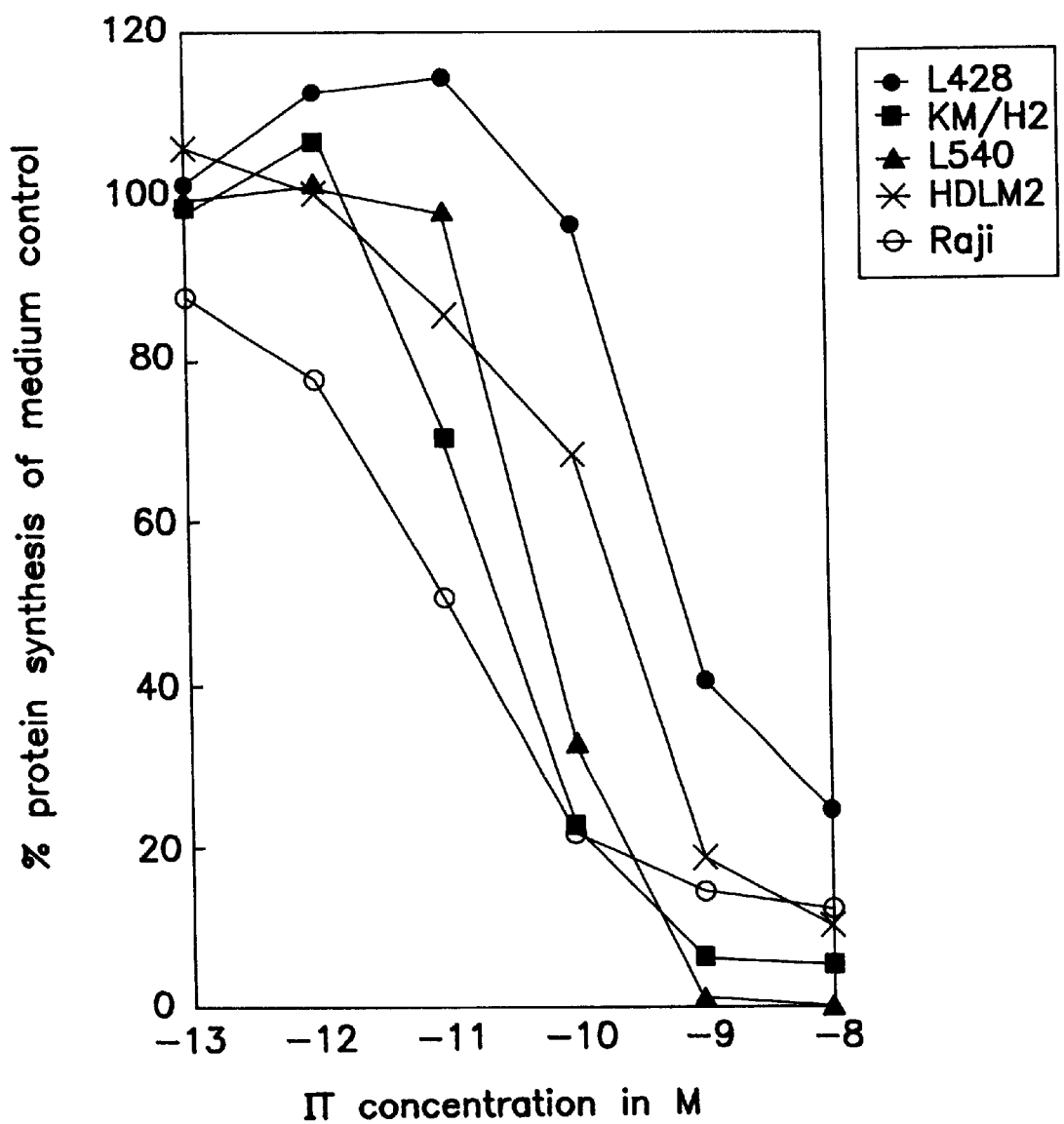

FIG. 6C: shows that the growth of the CD80 negative, CD86 positive L540 cells (closed triangles) can inhibited by incubation with CD86-Gelonin. The CD80 and CD86 positive cell lines L428 (closed circles), KM-H2 (closed squares) and Raji (open circles) are also killed by CD86 Gelonin in a dose dependent fashion.

Figure 7:
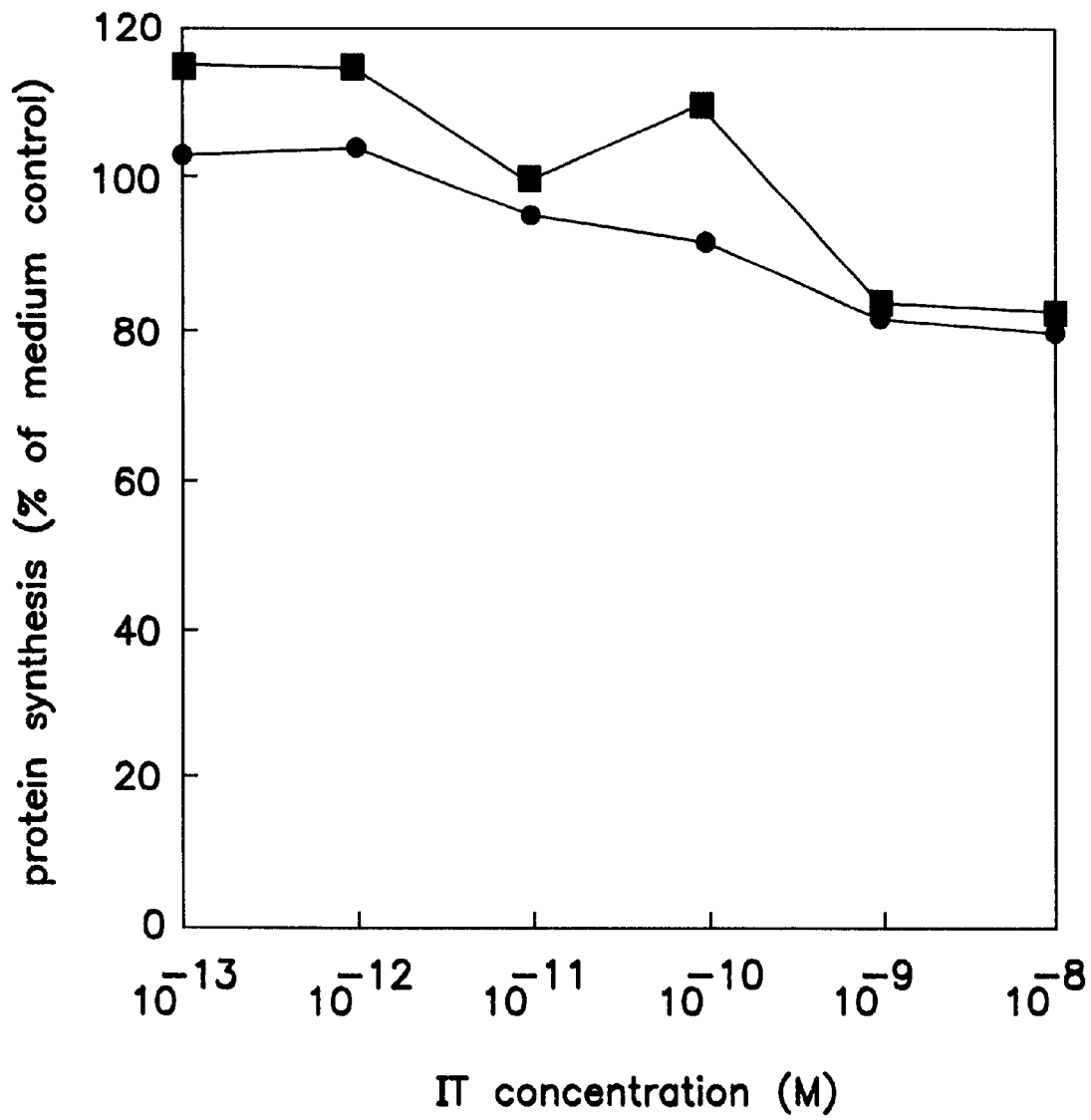

FIG. 7: demonstrates that cultured human umbilical vein endothelial cells (HUVECs) are not sensitive to CD80-Sap. The growth of HUVECs in the presence of CD80-Sap (closed squares) or the combination of free anti-CD80 Mab and free toxin (closed circles) is not significantly inhibited. This clearly demonstrates that immunotoxins based on anti-CD80 and anti-CD86 are extremely selective and exhibit low non-specific toxicity when used as therapeutic agents in vivo.

Table 1: shows the biochemical characterization and activity of the immunotoxins anti-CD80Saporin, anti-CD80-Gelonin and anti-CD86-Gelonin. The conjugation ratio (ratio Toxin/Mab) ranges from 0.73 to 3.14 mole of toxin per mole of Mab. Saporin and gelonin activity (expressed as the concentration needed at which 50% of the protein synthesis is inhibited) is retained sufficiently as determined on reticulocyte lysate and compared to free saporin and gelonin, respectively.

Table 2: shows that exposure of the mononuclear cells to CD80-Sap for only 15 min. is sufficient for a strong reduction in the proliferative capacity of the allo-reactive T cells in the mixed lymphocyte cultures. Incubation with the anti-CD80 monoclonal antibody or the free toxin alone did not result in significant inhibition of T-cell proliferation.

Table 3: shows the cytotoxic potency of CD80-Saporin on the outgrowth of CD80 positive clonogenic cells. With untreated Raji cells $0.9 \times 10^5$ clonogenic units were scored, untreated KM-H2 cells resulted in $1.0 \times 10^6$ clonogenic units. Treatment of the CD80 expressing Raji cells with CD80-Sap resulted in outgrowth of only $1 \times 10^2$ clonogenic units, which accounts for a 3 log kill. The combination of free anti-CD80 Mab and free toxin did not inhibit the clonogenic units. Treatment of the CD80 expressing KM-H2 cells with CD80-Sap resulted in outgrowth of only $0.6 \times 10^2$ clonogenic units, which accounts for a 4.3 log kill. Again, the combination of free anti-CD80 Mab and free toxin did not inhibit the clonogenic units.

Table 4: shows that CD71-Saporin directed to the transferrin receptor is extremely toxic for hemopoietic progenitor cells derived from human bone marrow. The addition of CD71-Saporin to human bone marrow cultures resulted in the complete abrogation of hemopoietic progenitor cells. The addition of CD80-Sap resulted in only a slight inhibition of colony growth of normal bone marrow hemopoietic progenitor cells. The same level of inhibition was observed in the presence of free Mab and free toxin.

DETAILED DESCRIPTION OF THE INVENTION

The invention described herein draws on previously published work and pending patent applications. By way of example, such work consists of scientific papers, patents or pending patent applications. All of these publications and applications, cited previously or below are hereby incorporated by reference:

Definitions

As used herein, the term "immunotoxin" refers to chimeric molecules in which a cell-binding monoclonal antibody or fragments thereof are coupled or fused to toxins or their subunits. The toxin portion of the immunotoxin can be derived form various sources, such plants or bacteria, but toxins of human origin or synthetic toxins (drugs) can been used as well. Immunotoxins as well their construction are reviewed above and are well known to the person skilled in the art.

The "toxin" moiety of the immunotoxins of the present invention may be any toxin known in the art and is preferably chosen from the following group: saprin, ricin (preferably A chain), abrin, diphteria toxin, Pseudomonas exotoxin, pokeweed antiviral protein, ribosome inactivating proteins such as saporin and gelonin, etc. For review see Ghetie and Vitetta (Current. Opinion Immunol. 6:707 (1994)).

Also any method of modification of known toxins known in the art to make these toxins less immunogenic can be applied to the production of immunotoxins of the present invention.

As used herein, the term "antibody" refers to polyclonal antibodies, monoclonal antibodies, humanized antibodies, single-chain antibodies, and fragments thereof such as $F_{ab}$, $F_{(ab')2}$, $F_v$, and other fragments which retain the antigen binding function and specificity of the parent antibody.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as $F_{ab}$, $F_{(ab')2}$, $F_v$, and others which retain the antigen binding function and specificity of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

As used herein, the term "humanized antibodies" means that at least a portion of the framework regions of an immunoglobulin are derived from human immunoglobulin sequences.

As used herein, the term "single chain antibodies" refer to antibodies prepared by determining the binding domains (both heavy and light chains) of a binding antibody, and supplying a linking moiety which permits preservation of the binding function. This forms, in essence, a radically abbreviated antibody, having only that part of the variable domain necessary for binding to the antigen. Determination and construction of single chain antibodies are described in U.S. Pat. No. 4,946,778 to Ladner et al.

As used herein, the terms "CD80" and "CD86" refer to human surface molecules as extensively reviewed above. For immunization purposes CD80 and CD86 antigen may be prepared by any technique known in the art.

Antibodies to human CD80 and/or human CD86 are known in the art. The present invention also contemplates a new use for such antibodies as detailed above.

Monoclonal antibodies 5B5D1 and 1G10H6D10 were prepared essentially as described in U.S. Pat. No. 5,397,703 or international application WO 94/01547.

Other anti-human CD80 or anti-human CD86 monoclonal antibodies of the invention may be prepared similarly, or essentially as follows. First, polyclonal antibodies are raised against the CD80 or CD86 antigen. Second, monoclonal antibodies specific for CD80 or CD86 are selected (more detailed below).

Alternatively, anti-human CD80 or anti-human CD86 monoclonal antibodies can be produced using impure CD80 or CD86 antigens as immunogens, provided that there is available a screening assay which distinguishes antibodies directed against other antigens present in the immunogenic composition. Also cells or membrane fractions containing the molecule of interest as immunogens may be used in order to preserve the conformational constraints provided by a membrane environment. Immunizing mice with whole cells usually yields a strong immune response which generates antibodies to a large number of different molecules. This broad immune response precludes the use of the immunogen cells in subsequent screening for specific antibody production by hybridoma clones derived from the mouse spleen or lymphocyte cells. Furthermore, when the antigen of interest is expressed at low density, it is likely that the frequency of mouse B cells specific for the antigen will be relatively low. This low frequency necessitates the screening of large numbers of hybridoma clones to identify a clone which produces antibodies directed against the antigen of interest.

General techniques for raising polyclonal sera and monoclonal antibodies are set out below:

a) Polyclonal Sera

Polyclonal sera may be prepared by conventional methods. In general, a solution containing the CD80 or CD86 antigen is first used to immunize a suitable animal, preferably a mouse, rat, rabbit or goat. Rabbits and goats are preferred for the preparation of polyclonal sera due to the volume of serum obtainable, and the availability of labeled anti-rabbit and antigoat antibodies. Immunization is generally performed by mixing or emulsifying the antigen-containing solution in saline, preferably in an adjuvant such as Freund's complete adjuvant, and injecting the mixture or emulsion parenterally (generally subcutaneously or intramuscularly). A dose of 50–200 $\mu$g/injection is typically sufficient. Immunization is generally boosted 2–6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization.

Polyclonal antisera are obtained by bleeding the immunized animal into a glass or plastic container, incubating the blood at 25° C. for one hour, followed by incubating at 4° C. for 2–18 hours. The serum is recovered by centrifugation (e.g., 1,000×g for 10 minutes). About 20–50 ml per bleed may be obtained from rabbits.

b) Monoclonal Antibodies

Monoclonal antibodies are prepared using the method of Kohler and Milstein, *Nature* (1975) 256:495–96, or a modification thereof. Typically, a mouse or rat is immunized as described above. However, rather than bleeding the animal to extract serum, the spleen (and optionally several large lymph nodes) are removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the desired immunizing cell-surface antigen (and which do not bind to unrelated antigens). The selected mAb-secreting hybridomas are then cultured either in vitro (e.g., in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}$P and $^{125}$I), electron-dense reagents, enzymes, and ligands having specific binding partners. Enzymes are typically detected by their activity. For example, horseradish peroxidase is usually detected by its ability to convert 3,3',5,5'-tetra-methylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}$I may serve as a radioactive label or as an electron-dense reagent. HRP may serve as enzyme or as antigen for a mAb. Further, one may combine various labels for desired effect. For example, mAbs and avidin also require labels in the practice of this invention: thus, one might label a mAb with biotin, and detect its presence with avidin labeled with $^{125}$I, or with an anti-biotin mAb labeled with HRP. Other permutations and possibilities will be readily apparent to those of ordinary skill in the art, and are considered as equivalents within the scope of the instant invention.

As used in the present invention, the term "conjugates" refers to the result from any type of conjugation (or fusion or coupling) between the toxin moiety and the antibody moiety which can be brought about by any technique known in the art. Such techniques include chemical bonding by any of a variety of well-known chemical procedures (by means of heterobifunctional cross-linkers such as SPDP, carbodiimide, glutaraldehyde, or the like). Such conjugates can be separated from non-conjugated material by any separation technique known in the art suitable for this purpose.

A preferred means of fusing the antibody part to the toxin part is by recombinant means such as through production of single chain antibodies which are recombinantly expressed as part of a longer polypeptide chain which also contains a toxin part. Recombinant immunotoxin produced in this way may be isolated by any technique known in the field of recombinant DNA expression technology suitable for this purpose.

As used herein, the term "vector" may comprise a plasmid, a cosmid, a phage, or a virus.

In order to carry out the expression of the single chain antibody-toxin moiety fusion polypeptides (also termed "recombinant immunotoxin") of the invention in bacteria such as *E. coli* or in eukaryotic cells such as in *S. cerevisiae*, or in cultured vertebrate or invertebrate hosts such as insect cells, Chinese Hamster Ovary (CHO), COS, BHK, and MDCK cells, the following steps are carried out:

transformation of an appropriate cellular host with a recombinant vector, in which a nucleotide sequence coding for the fusion protein has been inserted under the control of the appropriate regulatory elements, particularly a promoter recognized by the polymerases of the cellular host and, in the case of a prokaryotic host, an appropriate ribosome binding site (RBS), enabling the expression in said cellular host of said nucleotide sequence. In the case of an eukaryotic host any artificial signal sequence or pre/pro sequence might be provided, or the natural signal sequence might be employed, culture of said transformed cellular host under conditions enabling the expression of said insert.

As used herein, the expression "killing of the CD80 or CD86 expressing cells" is to be understood as implying an inhibition of protein synthesis resulting in elimination or death of these cells. Killing of the CD80 or CD86 expressing cells surprisingly also has an effect on the activation state of other cells as explained earlier.

As used herein, the expression "CD80 or CD86 expressing cells" is reviewed above. These surface antigens are mainly expressed an antigen presenting cells (APCs).

It should be clear that any type of cell expressing CD80 and/or CD86 may be envisaged for treatment with the immunotoxins or compositions comprising the same of the present invention. It should also be clear that the treatment envisaged by the present invention is particularly one which has an effect on a second cell type (T cell) which receives a signal from the first cell type (APC) mediated via the CD80 or CD86 molecules.

As used herein, the term "alloantigen" refers to foreign MHC antigens, recognized by specific T-cells and responsible for the onset of transplant rejection.

As used herein, the term "antigen presenting cells" refers to for instance human leukocyes, preferably macrophages, monocytes, dendritic cells, Langerhans cells or B cells.

As used herein, the term "composition" refers to any composition comprising as an active ingredient an immunotoxin according to the present invention possibly in the presence of suitable excipients known to the skilled man. The immunotoxins of the invention may thus be administrated in the form of any suitable compositions as detailed below by any suitable method of administration within the knowledge of a skilled person.

Formulations and Methods of Administration

The immunotoxins of this invention are administered at a concentration that is therapeutically effective to prevent allograft rejection, to treat autoimmune diseases, or to treat malignancies of lymphoid origin. To accomplish this goal, the immunotoxins may be formulated using a variety of acceptable excipients known in the art. Typically, the immunotoxins are administered by injection, either intravenously or intraperitoneally. Methods to accomplish this administration are known to those of ordinary skill in the art. It may also be possible to obtain compositions which may be topically or orally administered or in the form of an aerosol, or which may be capable of transmission across mucous membranes.

Before administration to patients, formulants may be added to the immunotoxins. A liquid formulation is preferred. For example, these formulants may include oils, polymers, vitamins, carbohydrates, amino acids, salts, buffers, albumin, surfactants, or bulking agents. Preferably carbohydrates include sugar or sugar alcohols such as mono, di, or polysaccharides, or water soluble glucans. The saccharide or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. Sucrose is most preferred. "Sugar alcohol" is defined as a $C_4$ to $C_8$ hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to the amount used as long as the sugar or sugar alcohol is soluble in the aqueous preparation. Preferably, the sugar or sugar alcohol concentration is between 1.0 w/v % and 7.0 wt/v %, more preferable between 2.0 and 6.0 w/v %. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Any physiological buffer may be used, but citrate, phosphate, succinate, and glutamate buffers or mixtures thereof are preferred. Most preferred is a citrate buffer. Preferably, the concentration is from 0.01 to 0.3 molar. Surfactants that can be added to the formulation are shown in EP Nos. 270,799 and 268,110.

Additionally, immunotoxins can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546 which are all hereby incorporated by reference in their entireties. Preferred polymers are polyoxyethylated polyols and polyethylene glycol (PEG). PEG is soluble in water at room temperature and has the general formula: $R(O\text{---}CH_2\text{---}CH_2)_n O\text{---}R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1,000 and 40,000, more preferably between 2,000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be vaned to achieve a covalently conjugated PEG/antibody of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, *J. Bio. Chem.* 263:15064–15070, and a discussion of POG/IL-2 conjugates is found in U.S. Pat. No. 4,766,106, both of which are hereby incorporated by reference in their entireties.

Another drug delivery system for increasing circulatory half-life is the liposome. Methods of preparing liposome delivery systems are discussed in Gabizon et al., *Cancer Research* (1982) 42:4734; Cafiso, *Biochem Biophys Acta* (1981) 649:129; and Szoka, *Ann Rev Biophys Eng* (1980) 9:467. Other drug delivery systems are known in the art and are described in, e.g., Poznansky et al., DRUG DELIVERY SYSTEMS (R. L. Juliano, ed., Oxford, N.Y. 1980), pp 253–315; M. L Poznansky, *Pharm Revs* (1984) 36:277.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

As stated above, the immunotoxins and compositions of this invention are used to prevent allograft rejection, to treat autoimmune diseases, or to treat malignancies of lymphoid origin. The preferred route of administration is parenterally. In parenteral administration, the compositions of this invention will be formulated in a unit dosage injectable form such as a solution, suspension or emulsion, in association with a pharmaceutically acceptable parenteral vehicle. Such vehicles are inherently nontoxic and nontherapeutic. Examples of such vehicles are saline, Ringer's solution, dextrose solution, and Hanks' solution. Nonaqueous vehicles such as fixed oils and ethyl oleate may also be used. A preferred vehicle is 5% dextrose in saline. The vehicle may contain minor amounts of additives such as substances that enhance isotonicity and chemical stability, including buffers and preservatives.

The dosage and mode of administration will depend on the individual. Generally, the compositions are administered so that the immunotoxins are given at a dose between 1 µg/kg and 10 mg/kg, more preferably between 10 µg/kg and 5 mg/kg, most preferably between 0.1 and 2 mg/kg. Preferably, it is given as a bolus dose. Continuous infusion may also be used. If so, the immunotoxins or composition comprising the same may be infused at a dose between 5 and 20 µg/kg/minute, more preferably between 7 and 15 µg/kg/minute.

According to the specific case, the "therapeutically effective amount" of the immunotoxins of the invention needed should be determined as being the amount sufficient to cure the patient in need of the treatment or at least to partially arrest the disease and its complications. Amounts effective for such use will depend on the severity of the disease and the general state of the patient's health. Single or multiple administrations may be required depending on the dosage and frequency as required and tolerated by the patient.

According to the embodiments of the present invention which involve treatment or prevention of transplant rejection, it should be stressed that the immunotoxins of the present invention or the compositions comprising the same may be administrated before, during and after the organ transplantation as is desired from case to case.

In case the immunotoxins or the compositions comprising the same are administered directly to the host, treatment will preferably start at the time of the transplantation and continue afterwards in order to kill CD80 or CD86 expressing cells and thus prevent the activation and differentiation of host T-cells against the MHC on the allograft.

In case the donor organ is ex vivo perfused with immunotoxins or the compositions comprising the same, treatment of the donor organ ex vivo will start before the time of the transplantation of the donor organ in order to kill CD80 or CD86 expressing cells in said donor organ and thus prevent the activation and differentiation of host T-cells against the MHC on the allograft.

In case of induction of alloantigen-specific tolerance, lymphocytes which have previously been incubated ex vivo with the immunotoxins of the invention or compositions comprising the same are preferably administered to the patients before receiving transplantation.

The present invention will now be illustrated by reference to the following examples which set forth particularly advantageous embodiments. However, it should be noted that these embodiments are illustrative and are not to be construed as restricting the invention in any way.

EXAMPLES

Materials and Methods

Cell Lines

Mouse 3T6 cells (3T6) and 3T6 cells expressing hybrid molecules of the HR (high responder) allelic form of human Fc RIIa (3T6-CD32 cells) were a gift of Dr. P. A. M. Warmerdam, Department of Experimental Immunology, University Hospital Utrecht, Utrecht, The Netherlands (Warmerdam et al. *J. Immunol.* (1991) 147:1338). These cell lines were transfected with the cDNA encoding the human CD80 molecule (3T6-CD80 and 3T6-CD32/CD80) (De Boer et al. *Eur. J. Immunol.* 22:3071 (1992)) Cells of the Burkitt lymphoma-derived B cell line Raji, Epstein-Barr virus transformed B cell lines BTL6, ARC and RPMI 6688, and the Reed Stemberg cell lines L540, L428, HDLML and KM/H2 were cultured in RPMI1640 supplemented with 10% heat-inactivated fetal calf serum (FCS), 2 mM L-glutamin, 100 IU/ml penicillin and 100 μg/ml streptomycin, in humidified air with 5% $CO_2$ at 37° C. Human umbilical vein endothelial cells were isolated from human umbilical vein and cultured as above, except for the FCS that was replaced with 10% heat-inactivated human AB serum. Hepatocytic cell line HepG2 and the epidermoid cell line A431, were cultured in Dulbecco's modified Eagle's medium supplemented with 10% heat-inactivated fetal calf serum (FCS), 2 mM L-glutamin, 100 IU/ml penicillin and 100 μpg/ml streptomycin, in humidified air with 5% $CO_2$ at 37° C.

Protein Synthesis Inhibition Assays

The cytotoxic effect of the immunotoxin on cells was assessed by measuring their ability to inhibit protein synthesis in a concentration-dependent way. Cells were seeded in a 96 wells round bottom plate and incubated with specific monoclonal antibody alone, monoclonal antibody and Saporin-labeled goat anti-mouse immunglobulins (GAM-Sap), GAM-Sap alone, or CD80-Sap, for various time intervals. Hereafter [$^3$H]-Leucine (1 μCi) was added to each well followed by an overnight incubation. Cells were harvested on glasswool filters and counted on a beta plate scanner. Cell numbers used were chosen so, that [$^3$H]-leucine incorporation was a linear function of the number of cells. Results were expressed as percentage $^3$H-leucine incorporation with regard to mock-treated cells. The $IC_{50}$ value is the concentration of immunotoxin needed to obtain 50% inhibition of leucine incorporation.

Ribosome inactivation activity of free and conjugated toxins was tested in a reticulocyte lysate system as described by Parente et al. (*Biochem Biophys Acta* 1216:43 (1993)).

Immunohistochemistry

Conventional histopathology on formalin-fixed paraffin-embedded tissue showed a normal "architecture". In addition a part of the specimens were snap frozen and stored at −20 C. Immunohistochemistry was done on frozen tissue sections of 6–8 μm thickness, after 10 min fixation in acetone at room temperature. The first incubation was done with mAb at predetermined optimal dilution (30', room temperature). The second and third incubation were performed with rabbit-anti-mouse immunoglobulin and sheep-anti-rabbit immunoglobulin, respectively, both conjugated to horseradish peroxidase (Dakopatts, Glostrup, Danmark). Color development was done with 3'3-diaminobenzidine tetrahydro-chloride and hydrogen peroxide as substrates. Sections were then counterstained with hematoxylin. Controls included replacement by an irrelevant antibody.

Flow Cytometric Analysis

Cells (0.1–0.2×10$^6$/sample) were incubated for 15' at 4° C. with the mAb (10 μg/ml). After washing twice in RPMI1640 supplemented with 10% FCS, the cells were incubated for another 15' at 4° C. with goat anti-mouse antibodies conjugated to fluorescein isothiocyanate (FITC) or phycoerythrin (PE). The cells were washed twice in RPMI1640 supplemented with 10% FCS and finally suspended in PBS supplemented with 1% BSA and 0.1% $NaN_3$ and analyzed with a FACScan flow cytometer (Becton Dickinson). The specific binding of the monoclonal antibodies is expressed as the mean fluorescent intensity in arbitrary units.

Clonogenic Assay

Series of 12 serial 5-fold dilutions (6 aliquots of 100 μl per dilution) were prepared from cell line Raji (starting concentrations 10$^6$, 10$^5$, 10$^4$ and 10$^3$ cells/ml) in 96-well flat-bottom plates. Subsequently 2.10$^5$ irradiated PBMC per well were added. Cells were incubated with medium, monoclonal antibody (mAb) and saporin (Sap) separately or with CD80-Sap at a concentration of 10$^{-8}$M in a total volume of 200 ul at 37° C. and 5% $CO_2$. After 14 days the plates were scored for colony outgrowth. The number of clonogenic units (CU) was calculated using a Spearman estimate as described by Johnson and Brown. The logarithmic kill of immunotoxin was determined by comparing the CU of treated and untreated cells.

Toxicity to Hematopoietic Progenitor Cells (HPC)

Bone marrow mononuclear cells were resuspended in RPMI 1640 containing 10% AB serum, 2 mM L-glutamin, 100 IU/ml penicillin and 100 μg/ml streptomycin with or without 10$^{-8}$ M anti-CD80 Saporin or Mab+Saporin separately. For the enumeration of colony-forming unit-granulcyte/macrophage (CFU-GM) colonies 100 unist/ml GM-CSF and 10 units/ml IL-3 were added, for burst-forming unit-erythroid (BFU-E) 3 units/ml erythropoietin (Epo) and for colony-forming unit-granulocyte/erythroid/macrophage/megakaryocyte (CFU-GEMM) 10 units/ml IL-3 and 3 units/ml Epo. Methylcellulose was added to a final concentration of 0.9%. Finally the cells (200,000) were plated out in 3 cm petri dishes and incubated at 37° C. and 5% $CO_2$. After 14 days colonies of >20 cells were counted.

Isolation of Human Monocytes

Buffy coats obtained after cytophoresis of healthy donors were used to prepare monocyte cultures. Mononuclear cell suspensions were obtained after buoyant density centrifugation. Monocytes were further enriched by the cold aggregation technique. Briefly the cell suspension was allowed to clump by low speed rotation at 4° C. Cell clumps were separated from the rest of the cells by centrifugation, this population was>89% CD14$^+$.

Purification of T cells

Peripheral blood mononuclear cells (PBMC) were isolated from buffy coat by density centrifugation. T cells were further purified by depletion of monocytes, B cells and NK cells using Lympho-Kwik T (One Lambda, Los Angeles, Calif.) according to the manufacturers protocol.

Mixed Lymphocyte Cultures

Peripheral blood mononuclear cells from two different donors (1×10$^5$/well) were cultured in 96-well round-bottom tissue culture plates. After 6 days of culture, cells were pulsed for 16 h with 0.5 μCi [$^3$H]-Thymidine, after which the cells were harvested using an automated cell harvester. [$^3$H]-Thymidine incorporation was determined with a liquid scintillation counter. Proliferation of T cells were performed in triplicate wells.

Antibodies

Anti-CD80 mAb 5B5D1 was generated by immunizing mice with insect cells expressing recombinant human CD80 as shown in Example 1 herein. Anti-CD86 mAb 1G10H6D10 was generated in a similar way by immunizing with insect cells expressing recombinant human CD86 as described in Example 2 herein.

EXAMPLE 1

Making Monoclonal Antibodies to CD80

A female BALB/c mouse was immunized (injected intraperitoneally) four times (i.e., at days 0, 28, 56 and 210) with Sf9 insect cells that were infected with a recombinant baculovirus containing a CD80 cDNA. Three days after the last injection, spleen cells were retrieved from the immunized mouse and used for cell fusion. Dissociated splenocytes from the immunized mouse were fused with SP2/0 murine myeloma cells at a ration of 10:3 using a polyethylene glycol/DMSO solution. The fused cells were resuspended in DMEM medium supplemented with hypoxanthine, thymidine, sodium pyruvate, glutamine, a nonessential amino acid solution, 10% inactivated fetal calf serum and 10% inactivated horse serum. The cells were then distributed to 960 wells on tissue culture plates to which aminoterin was added 24 hours after the cell fusion. Each well contained between 1 to 5 growing hybridoma clones at the average. After ten days, supernatants from the 960 primary wells were combined in groups of ten to form 96 pools for primary screening. The 96 pools were screened for the presence of specific antibody by FACS analysis using a CD80-expressing EBV-transformed human B cell line and yielded three positive pools. The thirty wells corresponding to the three positive pools were subjected to a second screening, using the FACS screening technique described above. This second screening provided three individual positive wells containing antibodies reactive with the CD80-expressing EBV-transformed human B cell line. The three positive wells were expanded and the cells were frozen. One positive well was subcloned and a stable hybridoma clone named 5B5D1 was obtained. This hybridoma clones secretes mouse antibodies of the IgG3 isotype.

Characterization of Anti-CD80 Monoclonal Antibody 5B5D1

The antibodies secreted by hybridoma clone 5B5D1 were tested for specific binding to the human CD80 molecule. Mouse 3T6 fibroblasts (3T6) and 3T6 cells stably transfected with the human CD80 molecule (3T6-CD80) were incubated with the supernatant of hybridoma clone 5B5D1 for 30 min at 4° C. Thereafter, the cells were separated from the supernatant, washed three times and incubated with FITC-labeled goat anti-(mouse IgG) antiserum (i.e. GAM-FITC). As a control, the cells were incubated with the GAM-FITC only. After another 3 washes, the cells were analysed for fluorescent staining using a FACScan instrument. FIG. 1, which summarizes the results of this experiment, shows that the antibodies secreted by the 5B5D1 hybridoma clone specifically bound to the CD80-expressing 3T6 cells as reflected by the gray bars, whereas 3T6 cells that did not express CD80 did not exhibit any binding significantly greater than that of the GAM-FITC as reflected by the white bars.

In another experiment Sf9 insect cells that were infected with a recombinant baculovirus containing a CD80 cDNA (Sf9CD80) and Sf9 insect cells that were infected with a recombinant baculovirus containing a CD86 cDNA (Sf9-CD86) were incubated with 1 µg 5B5D1 or 1 µg of the anti-CD86 monoclonal antibody 1G10H6D10, described below, for 30 min. at 4° C. Thereafter, the cells were separated from the supernatant, washed three times and incubated with FITC-labeled goat anti-(mouse IgG) antiserum (i.e. GAM-FITC) for 30 min. at 4° C. As a control, the cells were incubated with the GAM-FITC only. After another 3 washes, the cells were analysed for fluorescent staining using a FACScan instrument. FIG. 2, which summarizes the results of this experiment, shows that the antibodies secreted by the 5B5D1 hybridoma clone specifically bound to the CD80-expressing Sf9 cells as reflected by the gray bars, whereas Sf9 cells expressing the CD86 molecule did not exhibit any binding significantly greater than that of the GAM-FITC as reflected by the white bars. In contrast, the antibodies secreted by the 1G10H6D10 hybridoma clone specifically bound to the CD86-expressing Sf9 cells as reflected by the black bars, whereas Sf9 cells expressing the CD80 molecule did not exhibit any binding significantly greater than that of the GAM-FITC as reflected by the white bars.

EXAMPLE 2

Making Monoclonal Antibodies to CD86

A female BALB/c mouse was immunized (injected intraperitoneally) four times (i.e., at days 0, 28, 56 and 208) with Sf9 insect cells that were infected with a recombinant baculovirus containing a CD86 cDNA. Three days after the last injection, spleen cells were retrieved from the immunized mouse and used for cell fusion. Dissociated splenocytes from the immunized mouse were fused with SP2/0 murine myeloma cells at a ration of 10.3 using a polyethylene glycol/DMSO solution. The fused cells were resuspended in DMEM medium supplemented with hypoxanthine, thymidine, sodium pyruvate, glutamine, a non-essential amino acid solution, 10% inactivated fetal calf serum and 10% inactivated horse serum. The cells were then distributed to 960 wells on tissue culture plates to which aminoterin was added 24 hours after the cell fusion. Each well contained between 1 to 5 growing hybridoma clones at the average. After ten days, supernatants from the 960 primary wells were combined in groups of ten to form 96 pools for primary screening. The 96 pools were screened for the presence of specific antibody by FACS analysis using freshly isolated human monocytes from peripheral blood and yielded five positive pools. The fifty wells corresponding to the five positive pools were subjected to a second screening, with the FACS screening technique described above using freshly isolated human monocytes from peripheral blood and the CD86-expressing human EBV-transformed B cell line RPMI 6688. This second screening provided one individual positive wells containing antibodies reactive with the both human monocytes and the CD86-expressing EBV-transformed human B cell line RPMI 6688. This positive well was subcloned and a stable hybridoma clone named 1G10H6D10 was obtained. This hybridoma clones secretes mouse antibodies of the IgG1 isotype.

Characterization of Anti-CD86 Monoclonal Antibody 1G10H6D10

The antibodies secreted by hybridoma clone 1G10H6D10 were tested for specific binding to the human CD86 molecule. CD86-expressing EBV-transformed human B cells (RPMI 6688) and peripheral blood human T cells were incubated with the supernatant of hybridoma clone 1G10H6D10 or an isotype matched control monoclonal antibody (control mAb) for 30 min. at 4° C. Thereafter, the cells were separated from the supernatant, washed three times and incubated with FITC-labeled goat anti-(mouse IgG) antiserum (i.e. GAM-FITC). The cells were also incubated with the GAM-FITC alone. After another 3 washes, the cells were analysed for fluorescent staining using a FACScan instrument. FIG. 3, which summarizes the results of this experiment, shows that the antibodies secreted by the 1G10H6D10 hybridoma clone specifically bound to the CD86-expressing RPMI 6688 cells as reflected by the gray bars, whereas freshly isolated human peropheral blood T cells that did not express CD86 did not exhibit any binding significantly greater than that of the control monoclonal antibody as reflected by the black bars, or GAM-FITC as reflected by the white bars.

In the experiment described above in Example 1, Sf9 insect cells that were infected with a recombinant baculovirus containing a CD80 cDNA (Sf9CD80) and Sf9 insect cells that were infected with a recombinant baculovirus containing a CD86 were used to demonstrate that the antibodies secreted by hybridoma cone 1G10H6D10 are specific for CD86. FIG. 2 shows that the antibodies secreted by the hybridoma clone 1G10H6D10 specifically bound to the CD86-expressing Sf9 cells as reflected by the black bars, whereas Sf9 cells expressing the CD80 molecule did not exhibit any binding significantly greater than that of the GAM-FITC as reflected by the white bars.

EXAMPLE 3

Generation of Chemically Coupled Immunotoxins

Anti-CD80 and anti-CD86 immunotoxins (IT's) were prepared essentially according to the method described by Tazzari et al. (*Br J Haematol* 8:203 (1992)) and consisted of Mab conjugated to the type 1 ribosome-inactivating proteins saporin or gelonin. The Mab and the toxin were conjugated via a disulfide bond between added sulfhydryl (SH) groups. Briefly, SH groups were introduced separately in the Mab and in the toxin by 2-iminothiolane treatment. To obtain an optimal toxin/Mab ratio, the experimental conditions were chosen so, that per toxin or Mab molecule respectively 1 and 2 SH groups were introduced (respectively 1 and 0.6 mM 2-iminothiolane was added in 50 mM sodium-borate buffer, pH 9). To quantify the amount of toxin conjugated in the resulting IT, a trace of $^{125}$I-labelled saporin was added to the toxin solution. Ellman's reagent was added to determine the number of introduced SH groups and to protect the SH groups to avoid self conjugation of toxin or Mab. The excess of Ellman's reagent was removed by Sephadex G-25 gel filtration the modified toxin was reduced with 20 mM β-mercapto-ethanol to free its SH groups and separated from β-mercapto-ethanol by chromatography on a Sephadex G-25 column and was collected directly onto the unreduced derivatized Mab. After concentration, the conjugation was allowed to proceed for 16 hours at room temperature. The IT's were collected from this reaction mixture by gel filtration on Sephacryl S-200. Conjugation and all gel filtrations were performed in phosphate buffered saline, pH 7.5. The Mab and toxin content of the IT's was estimated by the absorbance at A280 and from the amount of radioactivity. The biochemical characterization of the IT's is shown in Table 1. Binding activity of the IT's was checked by means of a competition experiment with biotin labeled Mab and compared to the competition with free Mab.

FIG. 3 shows the specificity of the anti-CD80 and anti-CD86 gelonin immunotoxins (alpha CD80-IT and alpha CD86-IT). The ant-CD80 gelonin can kill the A431 cells transfected with human CD80, as determined by the inhibition of cell proliferation, but not A431 cells transfected with human CD86 or untransfected cells. The anti-CD86 gelonin can kill the A431 cells transfected with human CD86 but not A431 cells transfected with human CD80 or untransfected cells. A combination of anti-CD80 Mab, anti-CD86 Mab and free gelonin did not result in the killing of any of the A431 cells.

Generation of Recombinant Immunotoxins

An antibody comprises a distinct structural domain of ~110 amino acids, which with significant functional modifications is reiterated 12 times in the IgG molecule, a disulfide-linked assembly of two two-domain light chains and two four-domain heavy chains. Two of those domains, VH and VL, associate from separate chains to form the antigen combining site. It has been shown that these two domains can be expressed as a single chain, tethered together by a short flexible polypeptide linker in such a way that their native ability to associate and bind antigen is preserved (Bird et al., 1988; Huston et al., 1988). These single chain antigen-binding proteins (scFv) have a number of important advantages over conventional antibodies. Because scFv are only one sixth the size of intact MAb they have accelerated pharmacokinetics relative to the latter, particularly with respect to tissue and tumor penetration and plasma clearance. This is particularly advantageous in vivo for both therapy and diagnostic imaging. Their small size also makes them much easier to engineer, as will be described below. In place of the conventional antibodies, scFv genes can be fused to the coding sequences of a wide range of other effector proteins such as toxins to make bi-functional proteins of minimal size.

Anti-CD80 and anti-CD86 scFv-immunotoxins, are generated from the mRNA isolated form the hybridoma cell lines producing the monoclonal antibodies. Each V-region (VH and VL of both monoclonal antibodies) is converted to single chain form. ScFv genes are assembled from PCR-amplified VH- and VL-encoding fragments by mixing equimolar amounts of these with an equimolar amount of a third fragment which encodes the 15 residue linker, (gly4ser)$_3$, and which overlaps with framework 4 of VH and framework 1 of VL. The mixture is then converted to full-length scFv of the form VH-linker-VL by extending the overlaps by PCR. The product is then reamplified with primers containing convenient restriction sites for insertion into the expression vector, and also a small epitope tag at the C-terminus for convenient quantification of scFv protein by ELISA. The active scFv is subcloned into a vector which contains the coding sequence of gelonin at the 5' end of the scFv connected by a linker prepared Mom Shiga-like toxin (SLT). The SLT sequence, CHHHASRVARMASDEFPSMC, contains a disulfide-bounded peptide with a recognition site for trypsin-like proteases and resembles the cleavable disulfide loop of Pseudomonas exotoxin A and diphtheria toxin.

EXAMPLE 4

To test the capacity of the various IT's to inhibit the proliferation of T cells in mixed lymphocyte cultures, peripheral blood mononuclear cells were incubated with anti-CD80 immunotoxin (CD80-Sap), the free anti-CD80 Mab or the free toxin (Sap). After different time intervals, the cells were washed and recultured for a total duration of six days. After six days the proliferation of the alloreactive T cells was determined by [3H]-Thymidine incorporation as described above. Table 2, which summarizes the results of these experiments, shows that exposure of the lymphocytes to CD80-Sap for as short as 15 min. is sufficient for a strong reduction in the proliferative capacity of the alloreactive T cells. Free anti-CD80 or free toxin do not inhibit the T-cell proliferation. The reduction of T-cell proliferation with CD80-Sap is the result of the elimination of CD80-expressing professional antigen-presenting cells needed for the costimulation of T cells. This clearly demonstrates the advantages of using an anti-CD80 immunotoxin for immunosuppression, since addition of the free anti-CD80 Mab does not have such strong inhibitory effects. Similar results have been obtained with two other IT's directed against CD80 or CD86 (alpha CD80-Gelonin and alpha CD86 Gelonin). FIG. 4 shows that both anti CD80-Gelonin and anti-CD86-Gelonin can dose dependently inhibit the proliferation of alloreactive T cells during a mixed lymphocyte culture, whereas the free toxin only inhibits the proliferation of the T cells at high concentrations.

EXAMPLE 5

Expression of CD80 and CD86 on Reed-Stemberg Cells

Immunohistochemistry was done on lymph node sections of HD patients as described above. Both anti-CD80 and anti-CD86 monoclonal antibodies strongly reacted with Hodgkin/Reed-Stemberg cells. The expression of the CD80 and CD86 molecules was also investigated on samples of normal non-lymphoid tissues (stomach, duodenum, oesophagus, thyroid, liver, lung, kidney, heart, brain, and skin), to evaluate the possible in vivo reactivity. No binding of anti-CD80 and anti-CD86 monoclonal antibodies to these normal non-lymphoid tissues was found.

EXAMPLE 6

Reactivity and Toxic Activity of Anti-CD80 and Anti-CD86 Mabs and Immunotoxins to Cells and Cell Lines The anti-CD80 and anti-CD86 Mabs were tested for reactivity to various cell lines by FACS analysis. Cell lines were incubated with anti-CD80 or anti-CD86 Mab for 30 min. at 4° C. Thereafter, the cells were separated from the supernatant, washed three times and incubated with FITC-labeled goat anti-(mouse IgG) antiserum (i.e. GAM-FITC). After another 3 washes, the cells were analysed for fluorescent staining using a FACScan instrument. FIG. 5, which summarizes the results of this experiment, shows that the Burkitt lymphoma-derived B cell line Raji is positive for both CD80 and CD86 expression. The Hodgkin-derived Reed-Stemberg cell line L540 is negative for CD80 expression, but positive for CD86 expression. The Reed-Stemberg cell lines L428, HDLM2 and KM-H2 are positive for both CD80 and CD86 expression.

In another experiment it is shown that the capacity of specific IT's to inhibit the growth of cell lines in vitro is correlated with the expression of the specific ligand to which the antibody part of the IT is directed. Cell lines were incubated with anti-CD80-saporin IT (CD80-Sap), anti-CD80-gelonin IT (CD80-Gel) or anti-CD86-gelonin IT (CD86-Gel). After 48 hours protein synthesis was measured by 3H-leucine incorporation as described above. FIG. 6A shows that the growth of the CD80 negative, CD86 positive L540 cells is not inhibited by incubation with CD80-Sap. The CD80 and CD86 positive cell lines L428, KM-H2 and Raji are killed by CD80-Sap in a dose dependent fashion FIG. 6B shows that similar results were obtained with CD80-Gel. FIG. 6C shows that the growth of the CD80 negative, CD86 positive L540 cells can be inhibited by incubation with CD86-Gel. The CD80 and CD86 positive cell lines L428, KM-H2 and Raji are also killed by CD86-Gel in a dose dependent fashion.

In yet another experiment the cytotoxic potency of CD80-Sap on the outgrowth of CD80 positive clonogenic cells was tested in a clonogenic assay as described above. The results of this experiment are summarized in Table 3. Table 3 shows that with untreated Raji cells $0.9 \times 10^5$ clonogenic units were scored, untreated KM-H2 cells resulted in $1.0 \times 10^6$ clonogenic units. Treatment of CD80 expressing Raji cells with CD80-Sap resulted in outgrowth of only $1 \times 10^2$ clonogenic units, which accounts for a 3 log kill. The combination of free anti-CD80 Mab and free toxin did not inhibit the clonogenic units. Treatment of the CD80 expressing KM-H2 cells with CD80-Sap resulted in outgrowth of only $0.6 \times 10^2$ clonogenic units, which accounts for a 4.3 log kill. Again, the combination of free anti-CD80 Mab and free toxin did not inhibit the clonogenic units.

One concern with ligand directed immunotoxins is the toxicity of the immunotoxin for cells other than the target cells. This makes the generation of specific IT's for clinical use not obvious. This is demonstrated in an experiment summarized in Table 4. Table 4 demonstrated that an immunotoxin directed to the transferrin receptor (=CD71) is extremely toxic for hemopoietic progenitor cells derived from human bone marrow. The addition of CD71-IT to human bone marrow cultures as described above, resulted in the complete abrogation of hemopoietic progenitor cells.

The addition of CD80-Sap resulted in only a slight inhibition of colony growth of normal bone marrow hemopoietic progenitor cells. The same level of inhibition was observed in the presence of free Mab and free toxin. Similar results have been obtained using CD80-Gel and CD86 Gel. Another cell type sensitive for damage by IT's are endothelial cells. Damage to endothelial cells in vivo will result in a large toxicity. FIG. 7 demonstrates that cultured human umbilical vein endothelial cells (HUVECs) are not sensitive to CD80-Sap. The growth of HUVECs in the presence of CD80-Sap (closed squares) or the combination of free anti-CD80 Mab and free toxin (closed circles) is not significantly inhibited. This clearly demonstrates that immunotoxins based on anti-CD80 and anti-CD86 are extremely selective and exhibit low non-specific toxicity when used as therapeutic agents in vivo.

EXAMPLE 7

Induction of Donor Specific Tolerance in Heart and Kidney Transplantation

Peripheral blood mononuclear cells (PBMCs) from rhesus monkeys treated with recombinant anti-CD80-gelonin or anti-CD86-gelonin are tested for their ability to induce alloantigen-specific tolerance when transfused into an HLA mismatched recipient.

A kidney from the donor of the transfused PBMCs is transplanted into the tolerized recipient without giving cyclosporin A. The additional effect of perfusion of the kidney before transplantation with anti-CD80- or anti-CD86-saporin is determined.

EXAMPLE 8

Immunotherapy of Hodgkin's Disease with Anti-CD80 or Anti-CD86 Immunotoxin

The cytotoxic potency of recombinant anti-CD80 and anti-CD86 coupled to gelonin is tested. Single chain Fv (scFv) fragments of anti-CD80 and anti-CD86 monoclonal antibodies 5B5D1 and 1G10H6D10 are prepared. Recombinant anti-CD80 and/or anti-CD86 immunotoxin is prepared, as described in example 3, by fusing the nucleic acid sequence encoding variable domains of the respective antibodies to the nucleic acid encoding gelonin.

The resulting immunotoxins are compared in vitro for their capacity to block protein synthesis in a number of cell lines. The efficacity of these immunotoxins is also tested in clonogenic assays. The immunotoxins are tested in vivo, using immunodeficient mice with subcutaneous solid human tumor xenografts. Phase I clinical trials are performed with the best immunotoxin in chemotherapy resistant patients with advanced Hodgkin's disease.

Deposition of Cultures

The hybridomas used in the above examples, to illustrate the method of the present invention were deposited in and accepted by the European Collection of Cell Cultures, under the terms of the Budapest Treaty.

| Culture | Deposit Date | Accession No. |
| --- | --- | --- |
| 1G10H6D10 | June 2, 1995 | 95060210 |
| 5B5D1 | June 2, 1995 | 95060211 |

The present invention has been described with reference to specific embodiments. However, this application is intended to cover those changes and substitutions which may be made by those skilled in the art without departing from the spirit and the scope of the appended claims.

TABLE 1

Biochemical characterization and activity immunotoxins

|  | Ratio Toxin/MoAb | Activity* mg/ml** |
|---|---|---|
| free saporin | — | 1.8 |
| anti-CD80 × saporin | 0.73 | 3.2 |
| Gelonin | — | 20.0 |
| anti-CD80 gelonin | 3.14 | 28.2 |
| anti-CD86 gelonln | 2.73 | 44.7 |

Inhibition of cell-free protein synthesis, after reduction of the disulfide bond. The concentration is expressed at which 50% of the protein synthesis is inhibited.
As saporin or gelonin

TABLE 2

Inhibition of alloantigen-specific T-cell proliferation by treatment of peripheral blood lymphocytes with CD80-specific immunotoxin (CD80-Sap).

| Lymphocyte treatment conditions[§] | 15 min. exposure | | 60 min. exposure | | 24 hours exposure | |
|---|---|---|---|---|---|---|
| None | 35,969[¶] | (100%) | 37,808 | (100%) | 29,986 | (100%) |
| CD80 mAb | 34,688 | (96%) | 37,722 | (100%) | 26,756 | (89%) |
| Sap | 43,210 | (120%) | 33,770 | (89%) | 32,245 | (108%) |
| CD80-Sap | 13,768 | (38%) | 9,343 | (25%) | 4,800 | (11%) |

[§]Peripheral blood lymphocytes from two different donors were treated for the time duration indicated, with CD80-Sap or appropriate controls.
[¶]The proliferative capacity of the alloreactive T cells is expressed as the mean CPM of triplicate cultures, deterimed by [$^3$H]-Thymidine incorporation after 6 days of culture. The percentage of control (no treatment) is denoted between brackets.

TABLE 3

Influence of anti-CD80-Sap on the clonogenic growth of CD80 expressing

| | Raji | | KM/H2 | |
|---|---|---|---|---|
| Treatment | Clonogenic units | log-kill | Clonogenic units | log-kill |
| — | $0.9 \times 10^5$ | — | $1.0 \times 10^8$ | — |
| anti-CD80 + saporin | $1.0 \times 10^5$ | 0 | $1.2 \times 10^6$ | 0 |
| CD80-Sap | $1.0 \times 10^2$ | 3 | $0.6 \times 10^2$ | 4.3 |

TABLE 4

Influence of CD80-Sap treatment on hemopoletic progenitor cells from healthy human bone marrow.

|  | CFU-GEMM | CFU-GM | BFU-E |
|---|---|---|---|
| — | 100% | 100% | 100% |
| anti-CD80 + saporin | 85 ± 4 | 90 ± 10 | 74 ± 5 |
| CD80-Sap | 90 ± 5 | 94 ± 12 | 88 ± 10 |
| CD71-Sap | 0 | 0 | 0 |

Bone marrow mononuclear cells (n = 3) were incubated with either culture medium (−), free Mab with free saporin (anti-CD80 + saporin) or CD80-Sap. CD71-Sap, targeted to the transferrin receptor, was used as described in Materials and Methods. Due to the wide range of colonies found in the different samples, colony numbers are expressed as percentage of the number of the colonies found with culture medium.

What is claimed is:

1. A method for treating autoimmune diseases comprising administering to a patient in need of such treatment a therapeutically effective amount of an immunotoxin comprising an anti-human CD86 monoclonal antibody IG10H6D10 as deposited in the ECACC collection under No. 95060210 or a humanized antibody, a single-chain antibody or fragments and specificity of said monoclonal antibody, coupled to a toxin or active fragments thereof wherein the binding of the immunotoxin to CD86 results in the killing of the CD86 expressing cell.

2. A method for treating autoimmune diseases according to claim 1 wherein said antibody is a monoclonal antibody or a humanized antibody, a single chain antibody or fragments thereof which retain the antigen binding function and specificity of said monoclonal antibody.

3. The method of claim 1 wherein the autoimmune disease is rheumatoid arthritis.

4. The method of claim 1 wherein the autoimmune disease is systemic lupus erythematosus.

* * * * *